(12) United States Patent
Jimenez et al.

(10) Patent No.: US 10,357,232 B2
(45) Date of Patent: Jul. 23, 2019

(54) SYSTEMS FOR SEALING A TISSUE WALL PUNCTURE

(71) Applicant: APICA Cardiovascular Limited, Galway (IE)

(72) Inventors: Jorge H. Jimenez, Atlanta, GA (US); James L. Greene, Galway (IE); Peter J. Fitzgerald, Portola Valley, CA (US)

(73) Assignee: Apica Cardiovascular Limited, Galway (IE)

( * ) Notice: Subject to any disclaimer, the term of this patent is extended or adjusted under 35 U.S.C. 154(b) by 187 days.

(21) Appl. No.: 15/396,696

(22) Filed: Jan. 2, 2017

(65) Prior Publication Data
US 2017/0143320 A1    May 25, 2017

Related U.S. Application Data

(63) Continuation of application No. 13/949,619, filed on Jul. 24, 2013, now Pat. No. 9,532,773, which is a
(Continued)

(51) Int. Cl.
A61B 17/00    (2006.01)
A61B 17/064    (2006.01)
(Continued)

(52) U.S. Cl.
CPC ........ *A61B 17/0057* (2013.01); *A61B 17/064* (2013.01); *A61B 17/068* (2013.01); *A61B 2017/00575* (2013.01); *A61B 2017/00663* (2013.01); *A61B 2017/00668* (2013.01); *A61B 2017/0498* (2013.01);
(Continued)

(58) Field of Classification Search
CPC .............. A61B 17/0057; A61B 17/064; A61B 17/1214; A61B 2017/00575; A61B 2017/00592; A61B 2017/00597; A61B 2017/0061; A61B 2017/00615; A61B 2017/00637; A61B 2017/00672; A61B 2017/06076; A61B 2017/0649
See application file for complete search history.

(56) References Cited

U.S. PATENT DOCUMENTS 3,512,519 A    5/1970    Hall
3,540,451 A    11/1970    Zeman
(Continued)

FOREIGN PATENT DOCUMENTS

CA    2526920    2/2009
CN    1842354    10/2006
(Continued)

*Primary Examiner* — Todd J Scherbel
(74) *Attorney, Agent, or Firm* — Eversheds Sutherland (US) LLP

(57) ABSTRACT

Embodiments of the invention provide systems, apparatus, device and methods for sealing a puncture in a tissue wall. According to one aspect, the system includes at least one supporting element for insertion into or placement on at least a portion of a tissue wall proximate a puncture to prevent expansion of the puncture; and a closing element adapted for at least partial insertion into the tissue wall and shaped to compress at least a portion of a tissue wall in an inward direction to close the tissue puncture when inserted at least partially into the tissue wall.

15 Claims, 18 Drawing Sheets

Related U.S. Application Data continuation of application No. PCT/US2012/023142, filed on Jan. 30, 2012.

(60) Provisional application No. 61/437,247, filed on Jan. 28, 2011, provisional application No. 61/536,880, filed on Sep. 20, 2011.

(51) Int. Cl.
    *A61B 17/068*     (2006.01)
    *A61B 17/04*     (2006.01)
    *A61B 17/06*     (2006.01)

(52) U.S. Cl.
    CPC .............. *A61B 2017/0649* (2013.01); *A61B 2017/06052* (2013.01); *A61B 2017/06076* (2013.01)

(56) References Cited

U.S. PATENT DOCUMENTS

| | | | |
|---|---|---|---|
| 3,856,021 A | 12/1974 | McIntosh | |
| 4,204,541 A | 5/1980 | Kapitanov | |
| 4,366,819 A | 1/1983 | Kaster | |
| 4,769,031 A | 9/1988 | McGough et al. | |
| 4,904,264 A | 2/1990 | Scheunemann | |
| 4,955,856 A | 9/1990 | Phillips | |
| 5,098,369 A | 3/1992 | Heilman et al. | |
| 5,129,913 A | 7/1992 | Ruppert | |
| 5,139,517 A | 8/1992 | Corral | |
| 5,158,563 A | 10/1992 | Cosman | |
| 5,222,980 A | 6/1993 | Gealow | |
| 5,256,160 A | 10/1993 | Clement | |
| 5,291,179 A | 3/1994 | Ooe et al. | |
| 5,387,193 A | 2/1995 | Miraki | |
| 5,447,533 A | 9/1995 | Vachon et al. | |
| 5,456,714 A | 10/1995 | Owen | |
| 5,562,729 A | 10/1996 | Purdy et al. | |
| 5,577,993 A | 11/1996 | Zhu et al. | |
| 5,582,616 A | 12/1996 | Bolduc et al. | |
| 5,695,504 A | 12/1997 | Gifford et al. | |
| 5,728,116 A | 3/1998 | Rosenman | |
| 5,738,680 A | 4/1998 | Mueller et al. | |
| 5,755,697 A | 5/1998 | Jones et al. | |
| 5,782,844 A | 7/1998 | Yoon et al. | |
| 5,797,933 A | 8/1998 | Snow et al. | |
| 5,810,836 A | 9/1998 | Hussein et al. | |
| 5,810,851 A | 9/1998 | Yoon | |
| 5,814,005 A | 9/1998 | Barra et al. | |
| 5,824,070 A | 10/1998 | Jarvik | |
| 5,824,071 A | 10/1998 | Nelson et al. | |
| 5,827,316 A | 10/1998 | Young et al. | |
| 5,833,698 A | 11/1998 | Hinchliffe et al. | |
| 5,843,088 A | 12/1998 | Barra et al. | |
| 5,865,791 A | 2/1999 | Whyane et al. | |
| 5,893,369 A | 4/1999 | LeMole | |
| 5,910,153 A | 6/1999 | Mayenberger | |
| 5,924,424 A | 7/1999 | Stevens et al. | |
| 5,944,730 A | 8/1999 | Nobles et al. | |
| 5,976,174 A | 11/1999 | Ruiz | |
| 5,984,956 A | 11/1999 | Tweden et al. | |
| 5,989,278 A | 11/1999 | Mueller | |
| 6,001,056 A | 12/1999 | Jassawalla et al. | |
| 6,007,576 A | 12/1999 | McClellan | |
| 6,022,324 A | 2/2000 | Skinner | |
| 6,022,367 A | 2/2000 | Sherts | |
| 6,024,755 A | 2/2000 | Addis | |
| 6,039,748 A | 3/2000 | Savage et al. | |
| 6,066,085 A | 5/2000 | Heilman et al. | |
| 6,079,414 A | 6/2000 | Roth | |
| 6,080,173 A | 6/2000 | Williamson, IV et al. | |
| 6,080,176 A | 6/2000 | Young | |
| 6,113,611 A | 9/2000 | Allen et al. | |
| 6,146,325 A | 11/2000 | Lewis et al. | |
| 6,241,743 B1 | 6/2001 | Levin et al. | |
| 6,254,564 B1 | 7/2001 | Wilk et al. | |
| 6,267,732 B1 | 7/2001 | Heneveld et al. | |
| 6,273,862 B1 | 8/2001 | Privitera et al. | |
| 6,290,639 B1 | 9/2001 | Mussivand et al. | |
| 6,290,728 B1 | 9/2001 | Phelps et al. | |
| 6,346,071 B1 | 2/2002 | Mussivand | |
| 6,390,976 B1 | 5/2002 | Spence et al. | |
| 6,401,720 B1 | 6/2002 | Stevens et al. | |
| 6,409,739 B1 | 6/2002 | Nobles et al. | |
| 6,443,957 B1 | 9/2002 | Addis | |
| 6,458,140 B2 | 10/2002 | Akin et al. | |
| 6,506,197 B1 | 1/2003 | Rollero et al. | |
| 6,537,300 B2 | 3/2003 | Girton | |
| 6,551,319 B2 | 4/2003 | Lieberman | |
| 6,551,322 B1 | 4/2003 | Lieberman | |
| 6,551,332 B1 | 4/2003 | Nguyen et al. | |
| 6,589,277 B1 | 7/2003 | Fabiani et al. | |
| 6,607,541 B1 | 8/2003 | Gardiner et al. | |
| 6,638,237 B1 | 10/2003 | Guiles et al. | |
| 6,651,670 B2 | 11/2003 | Rapacki et al. | |
| 6,663,633 B1 | 12/2003 | Pierson, III | |
| 6,669,708 B1 | 12/2003 | Nissenbaum et al. | |
| 6,673,043 B1 | 1/2004 | Landesberg | |
| 6,676,678 B2 | 1/2004 | Gifford, III et al. | |
| 6,689,147 B1 | 2/2004 | Koster, Jr. | |
| 6,695,859 B1 | 2/2004 | Golden et al. | |
| 6,699,256 B1 | 3/2004 | Logan et al. | |
| 6,705,988 B2 | 3/2004 | Spence et al. | |
| 6,726,648 B2 | 4/2004 | Kaplon et al. | |
| 6,732,501 B2 | 5/2004 | Yu et al. | |
| 6,740,101 B2 | 5/2004 | Houser et al. | |
| 6,776,787 B2 | 8/2004 | Phung et al. | |
| 6,802,806 B2 | 10/2004 | McCarthy et al. | |
| 6,808,498 B2 | 10/2004 | Laroya et al. | |
| 6,824,071 B1 | 11/2004 | McMichael | |
| 6,827,683 B2 | 12/2004 | Otawara | |
| 6,863,677 B2 | 3/2005 | Breznock | |
| 6,869,437 B1 | 3/2005 | Hausen et al. | |
| 6,942,672 B2 | 9/2005 | Heilman et al. | |
| 6,978,176 B2 | 12/2005 | Lattouf | |
| 6,984,241 B2 | 1/2006 | Lubbers et al. | |
| 6,994,666 B2 | 2/2006 | Shannon et al. | |
| 7,018,384 B2 | 3/2006 | Skakoon | |
| 7,033,372 B1 | 4/2006 | Cahalan | |
| 7,048,681 B2 | 5/2006 | Tsubouchi et al. | |
| 7,056,286 B2 | 6/2006 | Ravenscroft et al. | |
| 7,077,801 B2 | 7/2006 | Haverich | |
| 7,083,631 B2 | 8/2006 | Houser et al. | |
| 7,163,525 B2 | 1/2007 | Franer | |
| 7,182,771 B1 | 2/2007 | Houser et al. | |
| 7,214,234 B2 | 5/2007 | Rapacki et al. | |
| 7,232,421 B1 | 6/2007 | Gambale et al. | |
| 7,258,694 B1 | 8/2007 | Choi et al. | |
| 7,309,343 B2 | 12/2007 | Vargas et al. | |
| 7,331,956 B2 | 2/2008 | Hovda et al. | |
| 7,404,792 B2 | 7/2008 | Spence et al. | |
| 7,510,561 B2 | 3/2009 | Beane et al. | |
| 7,637,919 B2 | 12/2009 | Ishikawa et al. | |
| 7,717,844 B2 | 5/2010 | Cohn | |
| 7,744,527 B2 | 6/2010 | Cohn | |
| 7,766,811 B2 | 8/2010 | Haverich | |
| 7,799,041 B2 | 9/2010 | Beane et al. | |
| 7,842,068 B2 | 11/2010 | Ginn | |
| 7,846,123 B2 | 12/2010 | Vassiliades et al. | |
| 7,846,179 B2 | 12/2010 | Belef et al. | |
| 7,931,581 B2 | 4/2011 | Cohn | |
| 7,942,805 B2 | 5/2011 | Shambaugh, Jr. | |
| 7,993,392 B2 | 8/2011 | Righini et al. | |
| 8,226,670 B2 | 7/2012 | Beane et al. | |
| 8,430,836 B2 | 4/2013 | Vassiliades et al. | |
| 8,556,930 B2 | 10/2013 | Ellingwood | |
| 8,579,790 B2 | 11/2013 | Jeffery et al. | |
| 8,764,795 B2 | 7/2014 | Whitman et al. | |
| 8,840,538 B2 | 9/2014 | Jeffery et al. | |
| 8,858,489 B2 | 10/2014 | Vassiliades et al. | |
| 2001/0051809 A1 | 12/2001 | Houser et al. | |
| 2002/0019623 A1 | 2/2002 | Altman et al. | |
| 2002/0019643 A1 | 2/2002 | Gifford et al. | |
| 2002/0032462 A1 | 3/2002 | Houser et al. | |

(56) References Cited

U.S. PATENT DOCUMENTS

| | | |
|---|---|---|
| 2002/0038127 A1 | 3/2002 | Blatter et al. |
| 2002/0045846 A1 | 4/2002 | Kaplon et al. |
| 2002/0055737 A1 | 5/2002 | Lieberman |
| 2002/0055738 A1 | 5/2002 | Lieberman |
| 2002/0055739 A1 | 5/2002 | Lieberman |
| 2002/0055740 A1 | 5/2002 | Lieberman |
| 2002/0055742 A1 | 5/2002 | Lieberman |
| 2002/0058958 A1 | 5/2002 | Walen |
| 2002/0095210 A1 | 7/2002 | Finnegan |
| 2002/0099394 A1 | 7/2002 | Houser et al. |
| 2002/0116018 A1 | 8/2002 | Stevens et al. |
| 2002/0177865 A1 | 11/2002 | McIntosh |
| 2002/0183786 A1 | 12/2002 | Girton |
| 2002/0193806 A1 | 12/2002 | Moenning et al. |
| 2003/0014064 A1 | 1/2003 | Blatter |
| 2003/0023255 A1 | 1/2003 | Miles et al. |
| 2003/0032979 A1 | 2/2003 | Mortier et al. |
| 2003/0040765 A1 | 2/2003 | Breznock |
| 2003/0045834 A1 | 3/2003 | Wing et al. |
| 2003/0078592 A1 | 4/2003 | Heilman et al. |
| 2003/0130668 A1 | 7/2003 | Nieman et al. |
| 2003/0181843 A1 | 9/2003 | Bibber et al. |
| 2003/0181913 A1 | 9/2003 | Lieberman |
| 2004/0002624 A1 | 1/2004 | Yu et al. |
| 2004/0050393 A1 | 3/2004 | Golden et al. |
| 2004/0068299 A1 | 4/2004 | Laske et al. |
| 2004/0073216 A1 | 4/2004 | Lieberman |
| 2004/0077989 A1 | 4/2004 | Goode et al. |
| 2004/0092858 A1 | 5/2004 | Wilson et al. |
| 2004/0097973 A1 | 5/2004 | Loshakove et al. |
| 2004/0097993 A1 | 5/2004 | Whayne |
| 2004/0098011 A1 | 5/2004 | Vargas et al. |
| 2004/0133155 A1 | 7/2004 | Varner et al. |
| 2004/0138702 A1 | 7/2004 | Peartree et al. |
| 2004/0153112 A1 | 8/2004 | Nissenbaum et al. |
| 2004/0158308 A1 | 8/2004 | Hogendijk et al. |
| 2004/0162608 A1 | 8/2004 | Haverich |
| 2004/0167547 A1 | 8/2004 | Beane et al. |
| 2004/0167551 A1 | 8/2004 | Gifford, III et al. |
| 2004/0171905 A1 | 9/2004 | Yu et al. |
| 2004/0186490 A1 | 9/2004 | Houser et al. |
| 2004/0225306 A1 | 11/2004 | Blatter et al. |
| 2004/0236170 A1 | 11/2004 | Kim |
| 2005/0033107 A1 | 2/2005 | Tsubouchi |
| 2005/0043781 A1 | 2/2005 | Foley |
| 2005/0075656 A1 | 4/2005 | Beaupre |
| 2005/0101982 A1 | 5/2005 | Ravenscroft et al. |
| 2005/0101983 A1 | 5/2005 | Loshakove et al. |
| 2005/0131451 A1 | 6/2005 | Kleshinski et al. |
| 2005/0137609 A1 | 6/2005 | Guiraudon |
| 2005/0149093 A1 | 7/2005 | Pokorney |
| 2005/0154411 A1 | 7/2005 | Breznock et al. |
| 2005/0171479 A1 | 8/2005 | Hruska et al. |
| 2005/0187568 A1 | 8/2005 | Klenk et al. |
| 2005/0192604 A1 | 9/2005 | Carson et al. |
| 2005/0209502 A1 | 9/2005 | Schmid et al. |
| 2005/0222582 A1 | 10/2005 | Wenchell |
| 2005/0251162 A1* | 11/2005 | Rothe .................. A61B 1/0014 606/153 |
| 2005/0251187 A1 | 11/2005 | Beane et al. |
| 2005/0256368 A1 | 11/2005 | Klenk et al. |
| 2005/0267495 A1 | 12/2005 | Ginn et al. |
| 2006/0020326 A9 | 1/2006 | Bolduc et al. |
| 2006/0036313 A1 | 2/2006 | Vassiliades et al. |
| 2006/0074484 A1 | 4/2006 | Huber |
| 2006/0089707 A1 | 4/2006 | Vassiliades et al. |
| 2006/0099716 A1 | 5/2006 | Tipler et al. |
| 2006/0142634 A1 | 6/2006 | Anstadt et al. |
| 2006/0161193 A1 | 7/2006 | Beane et al. |
| 2006/0167333 A1 | 7/2006 | Moore et al. |
| 2006/0178675 A1 | 8/2006 | Hamman |
| 2006/0241659 A1 | 10/2006 | Tulleken et al. |
| 2006/0259050 A1 | 11/2006 | DeWinter |
| 2007/0055357 A1 | 3/2007 | Pokorney et al. |
| 2007/0060952 A1 | 3/2007 | Roby et al. |
| 2007/0066943 A1 | 3/2007 | Prasad et al. |
| 2007/0088375 A1 | 4/2007 | Beane et al. |
| 2007/0100363 A1 | 5/2007 | Dollar et al. |
| 2007/0106315 A1 | 5/2007 | Gregoric et al. |
| 2007/0106328 A1 | 5/2007 | Wardle et al. |
| 2007/0112361 A1 | 5/2007 | Schonholz et al. |
| 2007/0167968 A1 | 7/2007 | Pandey |
| 2007/0167969 A1 | 7/2007 | Pandey |
| 2007/0173879 A1 | 7/2007 | Pandey |
| 2007/0197856 A1 | 8/2007 | Gellman et al. |
| 2007/0208214 A1 | 9/2007 | Hjelle et al. |
| 2007/0265643 A1 | 11/2007 | Beane et al. |
| 2008/0004640 A1 | 1/2008 | Ellingwood |
| 2008/0009668 A1 | 1/2008 | Cohn |
| 2008/0009887 A1 | 1/2008 | Cohn |
| 2008/0009891 A1 | 1/2008 | Cohn |
| 2008/0039883 A1 | 2/2008 | Nohilly |
| 2008/0058846 A1 | 3/2008 | Vosough |
| 2008/0076959 A1 | 3/2008 | Farnan et al. |
| 2008/0161826 A1 | 7/2008 | Guiraudon |
| 2008/0177301 A1 | 7/2008 | Svensson |
| 2008/0255597 A1 | 10/2008 | Pravong et al. |
| 2008/0269662 A1* | 10/2008 | Vassiliades ...... A61B 17/32053 604/8 |
| 2009/0012552 A1 | 1/2009 | Pandey et al. |
| 2009/0082778 A1 | 3/2009 | Beane et al. |
| 2009/0112062 A1 | 4/2009 | Bakos |
| 2009/0203957 A1 | 8/2009 | LaRose et al. |
| 2009/0204206 A1 | 8/2009 | Parquet et al. |
| 2009/0240264 A1 | 9/2009 | Tuval et al. |
| 2010/0004739 A1 | 1/2010 | Vesely |
| 2010/0010500 A1 | 1/2010 | Beane et al. |
| 2010/0010616 A1 | 1/2010 | Drews et al. |
| 2010/0049225 A1 | 2/2010 | To et al. |
| 2010/0087907 A1 | 4/2010 | Lattouf |
| 2010/0160847 A1 | 6/2010 | Braido et al. |
| 2010/0161040 A1 | 6/2010 | Braido et al. |
| 2010/0168778 A1 | 7/2010 | Braido |
| 2011/0092761 A1 | 4/2011 | Almog et al. |
| 2011/0106116 A1 | 5/2011 | Ducharme et al. |
| 2011/0118766 A1 | 5/2011 | Reichenbach et al. |
| 2011/0118770 A1 | 5/2011 | Pokorney et al. |
| 2011/0118833 A1 | 5/2011 | Nguyen et al. |
| 2011/0160850 A1 | 6/2011 | Bourque |
| 2011/0190811 A1 | 8/2011 | Shanley |
| 2011/0196190 A1 | 8/2011 | Farnan et al. |
| 2011/0224785 A1 | 9/2011 | Hacohen |
| 2011/0251450 A1 | 10/2011 | Pagani et al. |
| 2012/0059212 A1 | 3/2012 | LaRose et al. |
| 2012/0059457 A1 | 3/2012 | Leinsing et al. |
| 2012/0089181 A1 | 4/2012 | Shanley et al. |
| 2012/0123452 A1 | 5/2012 | Asfora et al. |
| 2012/0123461 A1 | 5/2012 | Gillies et al. |
| 2012/0226096 A1 | 9/2012 | Callaway et al. |
| 2012/0253386 A1 | 10/2012 | Rowe et al. |
| 2012/0296151 A1 | 11/2012 | Curtis et al. |
| 2012/0296358 A1 | 11/2012 | Nguyen et al. |
| 2013/0012761 A1 | 1/2013 | Gregoric et al. |
| 2013/0110228 A1 | 5/2013 | Braido |
| 2013/0116728 A1 | 5/2013 | Litvack et al. |
| 2013/0150654 A1 | 6/2013 | Stanfield et al. |
| 2013/0218169 A1 | 8/2013 | Vassiliades et al. |
| 2013/0253641 A1 | 9/2013 | Lattouf |
| 2014/0039375 A1 | 2/2014 | Jimenez et al. |
| 2014/0067057 A1 | 3/2014 | Callaway et al. |
| 2014/0100430 A1 | 4/2014 | Beane et al. |
| 2014/0148786 A1 | 5/2014 | Milo |
| 2014/0194833 A1 | 7/2014 | Andrus |
| 2014/0214159 A1 | 7/2014 | Vidlund et al. |
| 2014/0378772 A1 | 12/2014 | Sundt, III et al. |
| 2014/0379074 A1 | 12/2014 | Spence et al. |
| 2015/0032153 A1 | 1/2015 | Quadri et al. |
| 2015/0038770 A1 | 2/2015 | Colella |
| 2015/0112120 A1 | 4/2015 | Andrus |

(56) References Cited

U.S. PATENT DOCUMENTS

2015/0196321 A1 7/2015 Gregory et al.
2015/0359952 A1 12/2015 Andrus et al.
2016/0095705 A1 4/2016 Keranen et al.

FOREIGN PATENT DOCUMENTS

| | | |
|---|---|---|
| EP | 1 669 042 | 6/2006 |
| EP | 1 706 168 | 10/2006 |
| EP | 1 691 884 | 3/2011 |
| EP | 1 628 702 | 5/2013 |
| JP | 09-47457 | 2/1997 |
| JP | 11-500642 | 1/1999 |
| JP | 2002-518082 | 6/2002 |
| JP | 2006-518624 | 8/2006 |
| JP | 2007-510522 | 4/2007 |
| WO | 93/25148 | 12/1993 |
| WO | 96/25886 | 8/1996 |
| WO | 97/13463 | 4/1997 |
| WO | 99/65409 | 12/1999 |
| WO | 00/00193 | 1/2000 |
| WO | 00/15147 | 3/2000 |
| WO | 00/15149 | 3/2000 |
| WO | 00/41759 | 7/2000 |
| WO | 2000/074747 | 12/2000 |
| WO | 2003/001980 | 1/2003 |
| WO | 2004/026147 | 4/2004 |
| WO | 2004/096059 | 11/2004 |
| WO | 2005/046783 | 5/2005 |
| WO | 2006/019755 | 2/2006 |
| WO | 2006/020651 | 2/2006 |
| WO | 2006/093970 | 9/2006 |
| WO | 2007/038109 | 4/2007 |
| WO | 2007/047212 | 4/2007 |
| WO | 2007/047933 | 4/2007 |
| WO | 2007/117612 | 10/2007 |
| WO | 2008/131453 | 10/2008 |
| WO | 2008/153872 | 12/2008 |
| WO | 2009/100198 | 8/2009 |
| WO | 2009/117435 | 9/2009 |
| WO | 2012/025927 | 3/2012 |
| WO | 2012/040233 | 3/2012 |
| WO | 2012/103546 | 8/2012 |
| WO | 2012/106422 | 8/2012 |
| WO | 2013/064529 | 5/2013 |
| WO | 2013/189620 | 12/2013 |
| WO | 2015/109328 | 7/2015 |

* cited by examiner

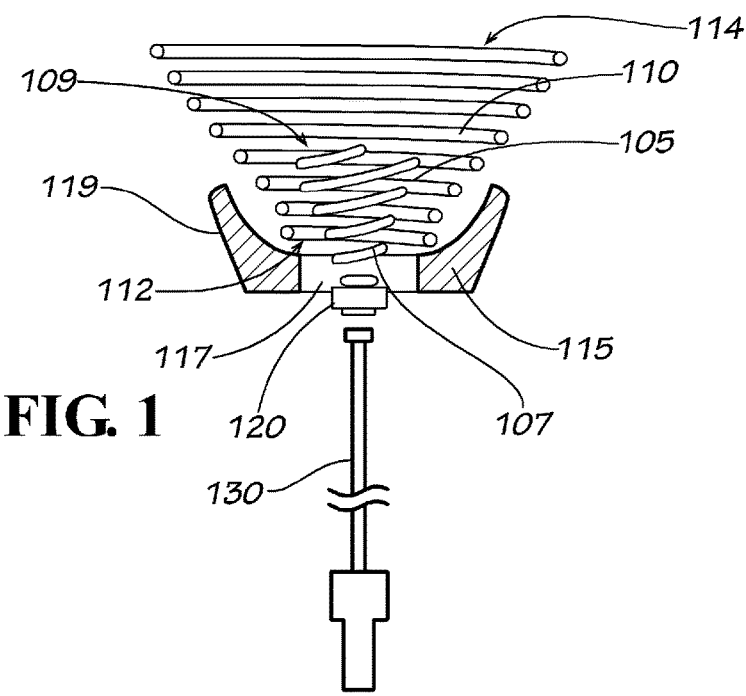
FIG. 1
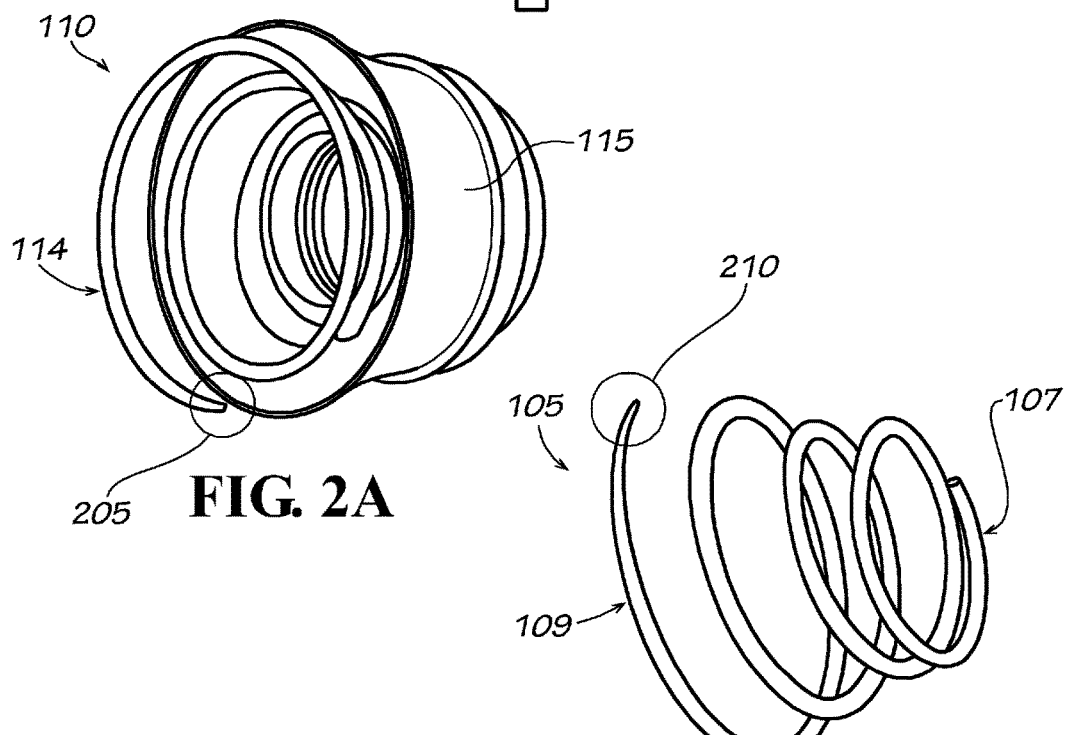
FIG. 2A
FIG. 2B

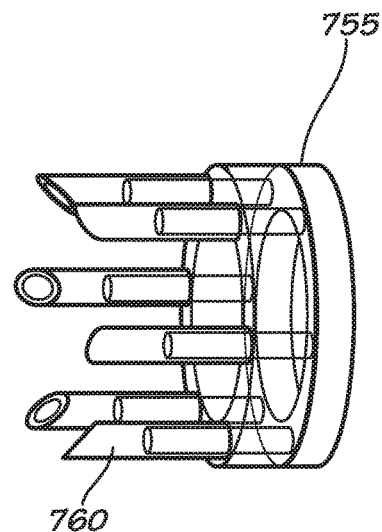
FIG. 10E
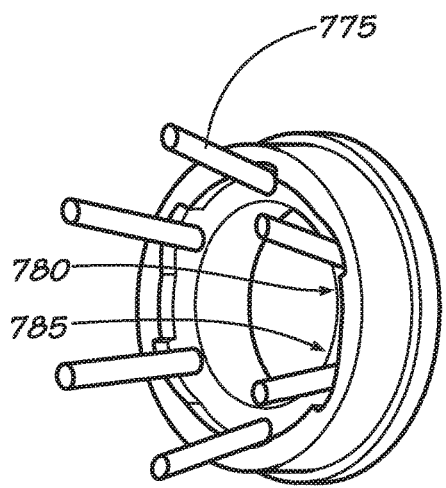 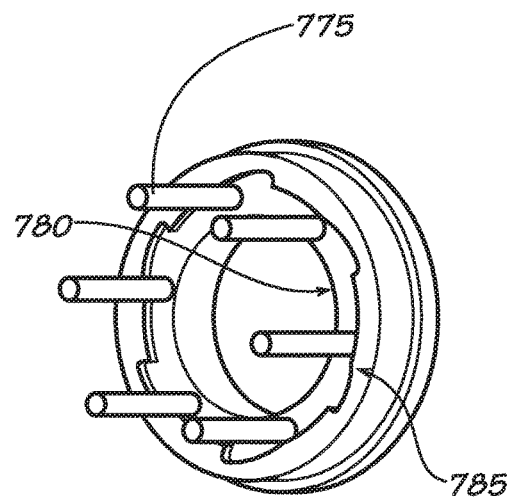
FIG. 10F  FIG. 10G

SYSTEMS FOR SEALING A TISSUE WALL PUNCTURE

CROSS-REFERENCE TO RELATED APPLICATIONS

This patent application is a continuation of U.S. application Ser. No. 13/949,619, filed Jul. 24, 2013, now U.S. Pat. No. 9,532,773, which is a continuation of PCT Application No. PCT/US2012/023142, filed Jan. 30, 2012, which claims priority benefit of U.S. Provisional Application Ser. No. 61/437,247 filed on Jan. 28, 2011 and U.S. Provisional Application Ser. No. 61/536,880 filed on Sep. 20, 2011, each of which is incorporated herein by reference in their entireties.

FIELD OF THE INVENTION

The present invention relates generally to tissue sealing devices, and particularly to systems, apparatus, and methods providing a device for sealing a tissue wall.

BACKGROUND OF THE INVENTION

Upon completion of clinical procedures, and occasionally during the procedure, a tissue access site is to be closed, either permanently or temporarily. For example, in some instances, it may be desirable to close a tissue wall puncture at least temporarily to monitor the patient's status or the effectiveness of the procedure performed. In doing so, a simple, quick, and effective means for closing or sealing a tissue puncture is desirable. Moreover, for temporary closure, it is further desirable for an easily removable sealing technique to allow simple removal prior to final closure of the puncture.

To reference as illustrative examples, cardiac surgery may utilize a conduit system, such as for use during procedures including, but not limited to, bypass, cardiac valve repair, cardiac valve replacement, attachment of a ventricular assist device, establishment of an apicoaortic conduit ("AAC"), and various combinations thereof. Intermediate conduit sealing may be called for during the procedure or thereafter. Such conduit systems can be used to create alternate outflow tracts in "off pump" procedures, which may effectively reduce and/or negate the detrimental effects of both cardiopulmonary by-pass ("CPB") and global cardiac ischemia, as well as avoiding vital areas of the heart, such as the conduction system, the native coronary arteries, and grafts from previous surgical revascularization. During a procedure utilizing a conduit system, a core or puncture is created through the tissue (e.g., the cardiac wall at or near the cardiac apex) and a conduit placed therethrough. The conduit thus provides access through the cardiac wall to the procedure site. In some instances, portions of the conduit may be removed and the cardiac tissue puncture is to be sealed or closed at least temporarily, such as for patient monitoring or during a change in procedure or instruments. It may be necessary for a surgeon to re-access the tissue, and for the conduit to be re-opened at the procedure site. Similar needs exist for procedures performed on other anatomical structures, and are not limited to cardiac procedures, such as gastric procedures requiring closure of the stomach and intestinal tissues to avoid gastro-intestinal drainage, prostate procedures to seal the prostrate during intervention, laparoscopic procedures to (temporarily or permanently) close trocar entry sites, and neurologic procedures to control drainage or to close access or wound sites near or within the cephalic cavity, for example.

Certain related devices and conduits have been previously described, such as those described in U.S. Pat. No. 7,846,123, which is incorporated by reference herein in its entirety. However, improved systems for closing and sealing a tissue puncture are desirable, which may optionally be utilized to provide temporary closure for later access.

SUMMARY OF THE INVENTION

Embodiments of the invention provide systems, apparatus, and methods using a device for sealing a tissue wall.

According to one aspect, a system for closing tissue is provided. The system may include: at least one supporting element for insertion into or placement on at least a portion of a tissue wall proximate a puncture to prevent expansion of the puncture; and a closing element adapted for at least partial insertion into the tissue wall and shaped to compress at least a portion of a tissue wall in an inward direction to close the puncture when inserted at least partially into the tissue wall.

According to another aspect, a system for closing tissue is provided that includes a coiled closure device. The coiled closure device may have a coil with a proximal end, a distal end, and defining a length therebetween. The coil may have an increasing radius increasing toward the distal end along at least a portion of the length of the coil. The increasing radius is adapted to compress at least a portion of a tissue wall in an inward radial direction when the coil is inserted at least partially into a tissue wall.

According to another aspect, a system for closing tissue is provided that includes at least one supporting element for insertion into or placement on at least a portion of a tissue wall proximate a cut or puncture to prevent expansion of the cut or puncture (generally referred to as a "puncture" herein), as well as an inner coil. The inner coil has a proximal end, a distal end, and defining a length therebetween. The inner coil may have an increasing radius increasing toward the distal end along at least a portion of the length of the coil. The increasing radius is adapted to compress at least a portion of a tissue wall in an inward radial direction when the coil is inserted at least partially into a tissue wall.

According to one embodiment, the supporting element can be an outer coil adapted for insertion through at least a portion of the tissue wall and at least partially surrounding the puncture, which may be substantially cylindrical in shape or which may have an increasing radius increasing toward its distal end. According to another embodiment, the supporting element may be at least one of: (a) a pin, (b) a suture, (c) an adhesive member, (d) a mesh member, (e) a clip, (f) a compressive band, (g) a bandage, (h) a flange, or (i) a suction member.

According to alternative embodiments, the supporting element, inner coil or outer coil can be collapsible and reversibly expandable for protected percutaneous or intravascular delivery. According to alternative embodiments, the invention also provides mechanisms for remotely detecting the depth of tissue penetration and proper sealing of the tissue and conduit.

According to yet another aspect, a system for closing tissue using a coil is provided. The system may include a coil member having a proximal end, a distal end, and defining a length therebetween. The coil member may include a hollow bore formed through the coil member and suture releasable insertable through the hollow bore of the coil member. Upon extracting the coil member through a tissue wall after insertion therein, at least a portion of the suture remains within the tissue wall to facilitate closing a puncture.

BRIEF DESCRIPTION OF THE DRAWINGS

Reference will now be made to the accompanying drawings, which are not necessarily drawn to scale, and wherein:

FIG. 1 illustrates a cross-sectional view of an outer coil and a coiled closure device positioned within the outer coil, in accordance with one embodiment of the invention.

FIGS. 2A-2E illustrate perspective views of outer coil and inner coiled closure devices, in accordance with various embodiment of the invention.

FIGS. 10A-10J illustrate perspective views of alternative attachment and closure systems, in accordance with various embodiments of the invention.

DETAILED DESCRIPTION OF THE INVENTION

Figures 2C, 2D:
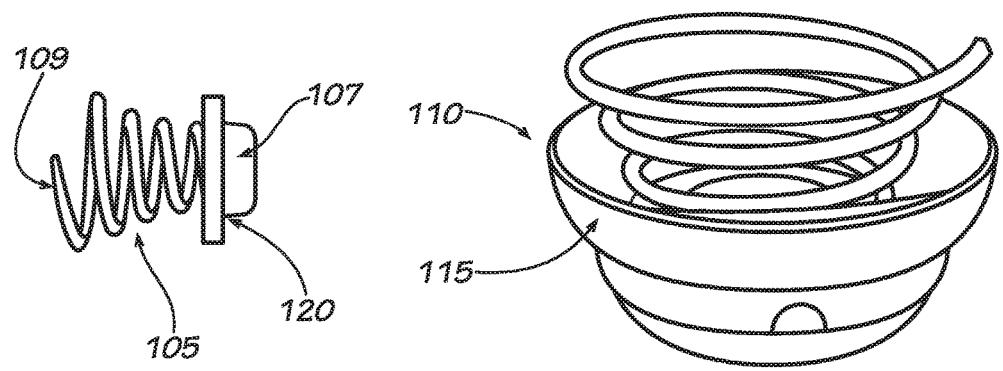

Embodiments of the invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. The singular forms "a," "an," and "the" can refer to plural instances unless context clearly dictates otherwise or unless explicitly stated.

Embodiments described herein provide systems, apparatus, and methods using a closure device for sealing a tissue wall. Embodiments may rely, in part, on the material characteristics of tissue to allow for closure and sealing, such as their geometry and/or elastic properties, utilized in combination with the tissue and puncture site anatomy. Most soft tissues in the body are elastic, viscoelastic, and/or quasilinearelastic in nature, and, therefore, highly deformable under external loads or forces. Areas of cut, punctured, or disrupted tissue may therefore be deformed so as to bring the severed areas of tissue together to induce closure. According to one embodiment, the closure device may include one or more coiled closure devices that, when rotated through the tissue, create an inward force on the tissue at or near a puncture site. According to other embodiments, however, one or more elements of the closure device may not be coiled, but instead other geometries which either stabilize or cause inward pressure, forcing the tissue to close at the puncture site.

Additional sealing of tissue, such as when tissue retains fluids and/or is under pressure, may be attained by deforming the tissue even further so that compression between surfaces of the tissue will seal the puncture site. For example, in some instances, a tissue wall may be retaining pressurized fluid, which, when the tissue is punctured or cut, the internal pressure will push severed tissue surfaces apart. In response, various embodiments described herein utilize an initial stabilizing device or element (also referred to herein interchangeably as a supporting device or element, or a securing device or element) before the incision or puncture is made through the tissue, to prevent the internal pressure from increasing the size of the incision or separate the severed wall. When using an initial stabilizing device, a secondary closure device may be smaller in size and operate cooperatively with the stabilizing device.

In one example embodiment, a closure device (also referred to herein interchangeably as a closure element or a closing device or closing element) may be a coiled closure device (also referred to herein with respect to certain embodiments as an "inner coil"), which may be rotatably inserted through a tissue wall, oriented to at least partially surround a puncture through the tissue wall, to at least partially close or seal the puncture. The coil can be formed with an increasing radius increasing in the direction toward its distal end (e.g., the end first inserted into the tissue wall). Rotating the widest end (the distal end) of the coil along a helical path through the tissue wall acts to compress at least a portion of the tissue wall surrounding the puncture radially inwards because the successive coil segments have a decreasing radius, which results in sealing the puncture due to the inward compression of the tissue. The coiled closure device can be utilized alone, or with another outer coil or with another supporting element serving to prevent further expansion or tearing of the tissue wall.

As described, other closure device or closure element embodiments may not utilize a coil. For example, instead of a coil, a closure device may include one or more pins or members extending through the puncture site tissue that urge tissue inward to seal the puncture site. In another embodiment, a closure device may include a flange that forms a suctioning force on the external surface of the tissue surrounding the puncture site, which serves to compress the puncture site tissue inward or at least maintain its current size without further expanding, such as when under pressure and/or manipulated during the clinical procedure being performed. Other embodiments may include clips, bands or other supporting elements to support the tissue wall during the clinical procedure and/or when inserting another closure device member, such as a coiled closure device or pinned closure device.

Therefore, the present invention provides a device, method and system for closing a tissue puncture, comprising: at least one supporting element for insertion into or placement on at least a portion of a tissue wall proximate a puncture to prevent expansion of the puncture; and a closing element adapted for at least partial insertion into the tissue wall, sized and shaped to compress at least a portion of the tissue wall in an inward direction to close the puncture when inserted at least partially into the tissue wall. In certain embodiments, the at least one supporting element is sized and shaped to compress at least a portion of the tissue wall in an inward radial direction. In certain embodiments, the at least one supporting element is sized and shaped to stabilize the tissue wall by at least partially preventing deflection or tearing of the tissue wall.

In certain embodiments, the closing element comprises at least one of a coiled element, a pinned element, or a compressive band. In certain embodiments, the at least one supporting element comprises at least one of a coil, a pin, a suture, an adhesive member, a mesh member, a clip, a compressive band, a bandage, a flange, or a suction member.

In certain embodiments, the supporting element comprises an outer coil adapted for insertion through at least a portion of the tissue wall and at least partially surrounding the puncture, and the closing element comprises an inner coil having an inner coil having a proximal end, a distal end, and defining a length therebetween, wherein the inner coil has an increasing radius increasing toward the distal end along at least a portion of the length of the inner coil, wherein the increasing radius of the inner coil is adapted to compress at least a portion of a tissue wall in an inward radial direction to close the puncture when the coil is inserted at least partially into the tissue wall.

In certain embodiments, the outer coil has an proximal end, and defines a length therebetween, wherein the outer coil has an increasing radius increasing toward the distal end along at least a portion of the length of the outer coil. In certain embodiments, the inner coil further comprises an engagement element proximate the proximal end adapted to releasably receive a delivery instrument for rotating the coil during insertion and removal.

In certain embodiments, the system and device further comprises a delivery instrument having an end adapted for releasable insertion into the engagement element of the inner coil. In certain embodiments, the delivery instrument has a release mechanism to prevent over insertion of the inner coil based on a pre-selected torque or a displacement mechanism.

In certain embodiments, the inner coil is adapted for insertion into a cardiac tissue for closing a puncture formed therethrough. In certain embodiments, the supporting element or the closing element include a delivery depth indicator system. In certain embodiments, the delivery depth indicator system comprises radio opaque or fluoroscopic elements which deform upon tissue contact. In certain embodiments, the delivery depth indicator system comprise electrodes which complete a circuit and transmit a signal upon tissue contact.

In certain embodiments, the outer coil or the inner coil includes a hollow bore formed therein and a releasable suture insertable through the hollow bore, wherein upon extracting the coil member through a tissue wall after insertion therein, at least a portion of the suture remains within the tissue wall to facilitate closing a puncture. In certain embodiments, the delivery instrument comprises a sheath for retractably protecting the coil from puncturing tissue.

In certain embodiments, the supporting member or the closing element comprises an electrode element capable of sensing an electronic signal from the tissue or delivering an electronic signal to the tissue. In certain embodiments, the closing element comprises a centering member extending distally at least partially through a center of the closing element.

In certain embodiments, the invention provides a system for closing a cardiac tissue puncture, comprising: at least one supporting element for insertion into or placement on at least a portion of a cardiac tissue wall proximate a puncture to prevent expansion of the puncture; and a closing element adapted for insertion into or placement on at least a portion of a cardiac tissue wall, and sized and shaped to compress at least a portion of a tissue wall in coordination with the supporting element in an inward direction to close the puncture. In certain embodiments, the supporting element comprises three or more pins disposed through the tissue to encompass the puncture, and the closing element comprises one or more compressive bands, wherein the one or more bands are each adapted to encompass at least three pins to compress the tissue inward towards the puncture.

The invention provides alternative embodiments of a system for closing tissue, comprising: at least one supporting element for insertion into or placement on at least a portion of a tissue wall proximate a puncture to prevent expansion of the puncture, sized and shaped to compress at least a portion of the tissue wall in an inward radial direction; and a closing element adapted for at least partial insertion into the tissue wall, and sized and shaped to stabilize the tissue wall by at least partially preventing deflection or tearing of the tissue wall.

The invention provides methods of sealing a puncture in a tissue wall, and a apical cardiac tissue wall in particular, comprising stabilizing the tissue surrounding the puncture with a supporting element and compressing the tissue inward to seal the puncture with a separate closing element. The various closure devices and elements described herein may be utilized as an accompaniment with any number of surgical procedures to close tissue punctures in a variety of possible tissues. For example, the closure devices may be utilized upon removal of a conduit providing fluid access across a tissue wall, such as, but not limited to, upon establishing an AAC, upon establishing a port for interventricular repairs (e.g., valve repair, valve replacement, or ablation procedures, etc.), upon establishing valved and/or open conduits (including bypass conduits) to augment native blood vessels in order to treat a variety of vascular conditions (e.g., aortic valvular disease, congestive heart failure, left ventricle outflow tract obstructions ("LVOTO"), peripheral arterial obstructions, small vessel obstructions, etc.), upon providing a conduit across a urinary bladder wall, upon providing a conduit across a gall bladder wall, upon providing a conduit into a thoracic cavity, upon providing a conduit into an abdominal cavity, upon providing a conduit into a cecal cavity, or upon providing access across or into any other tissue wall structures. Accordingly, the closure devices described herein may be utilized with any of the aforementioned procedures and/or to seal any of the aforementioned tissue walls.

FIG. 1 illustrates a cross-sectional view, and FIGS. 2A-2E illustrate alternative views, of embodiments of a coiled closure device that includes an outer coil and an inner coiled closure device positioned within the outer coil, in accordance with the invention. A coiled closure device 105 (inner coil) is positioned within an outer coil 110 attachment or stabilizing device, such as when the outer coil 110 is utilized to prevent the tissue wall from further expanding a puncture site and/or for use in securing a conduit within the puncture of the tissue wall. For example, in the embodiment shown, the outer coil 110 may serve as an attaching device that is advanced at least partially through a tissue wall and which becomes disposed at least partially between a first surface (e.g., an outer surface) and a second surface (e.g., an inner surface) of the tissue wall as the outer coil 110 is rotated. According to this embodiment, the outer coil 110 has a proximal end 112 and a distal end 114, and is formed as a radially-expanding helical coil that has an increasing radius that increases toward its distal end 114, which as shown in this embodiment may also be described as being a "conical coil." Thus, a radially expanding outer coil 110 can act to compress at least a portion of the tissue wall radially inwards when inserted therethrough by rotating. Compressing the tissue wall radially inwards may be utilized to compress tissue against a conduit positioned within the approximate center of the outer coil 110 to secure the conduit within the tissue wall, according to one embodiment. Moreover, as stated, the outer coil 110 can provide further support and reinforcement to the tissue wall to prevent further tearing or expansion of a proximate puncture site.

The outer coil 110 may further include a flange 115 extending from its approximate proximal end 112. The flange 115 includes an opening 117 defined through its approximate center. The flange also may include an extending body 119 that is shaped and sized to abut the tissue wall into which the outer coil 110 is intended to be inserted, according to one embodiment. In this embodiment, the extending body 119 of the flange 115 may be formed in an approximately frusto-conical shape adapted for receiving at least a portion of the tissue wall, such as if the intended tissue wall has a curved shape, allowing the formation of a substantially fluid-tight seal between the extending body 119 of the flange 115. In other embodiments, however, the flange 115 may be formed according to a number of different geometries, which may be selected depending upon the intended anatomy into which the outer coil 110 is to be implanted. Other geometries include, but are not limited to, hemispherical (e.g., for a curved tissue wall), substantially flat or annular-shaped (e.g., for a substantially flat tissue wall), or any of the aforementioned geometries formed in an opposite configuration such that the members 119 of the flange 115 extend in the proximal direction instead of in the distal direction (e.g., if the tissue is curved in the opposite direction of that illustrated by FIG. 2E).

It is appreciated that the flange 115, or a portion thereof, may be formed from a rigid, partially rigid, biodegradable or elastomeric material, allowing the flange 115 either to cause the tissue wall to substantially conform to the flange geometry or allowing the flange 115 to substantially conform to the tissue wall geometry. The opening 117 of the flange 115 can be of any size and shape, such as may be adapted for receiving a conduit and/or any other surgical instruments therethrough. In addition, the flange opening 117 is also sized to allow the coiled closure device 105 (the inner coil) to fit therethrough during insertion of the coiled closure device 105 into at least a portion of the tissue wall prior to removal of the outer coil 110 (if removed at all). It is appreciated that, according to other embodiments, a closure device may not include an outer coil, and may optionally include a different means to urge the puncture site tissue inward, such as the embodiments described below with reference to FIGS. 10A-10I. The flange may also have orifices or ducts which permit the passage of a fluid, such ducts may be used to apply positive or negative air or fluid pressure on the tissue through the flange, such as vacuum-assisted suction in order to stabilized the surface of the flange on the surface of the tissue.

The coiled closure device 105 likewise has a proximal end 107 and a distal end 109, and as shown can be formed as a radially-expanding helical coil that has an increasing radius that increases toward its distal end 109. Like the outer coil 110, the radially expanding coiled closure device 105 compresses at least a portion of the tissue wall in an inward radial direction when inserted through the tissue wall by rotating. Compressing the tissue wall radially inwards allows closing the tissue puncture on itself and substantially sealing the tissue puncture. The coil 105 shown in FIGS. 1 and 2C has an engagement element 120 at the proximal end 107 which serves as a plug or cap to further seal the tissue. As will be discussed more fully below, the proximal surface of the engagement element of the closure device can be configured for maneuverability engagement, either manually or mechanically, with a delivery tool, and the distal aspect of the engagement element can be flat, elongated, angled, threaded, valved or flanged for sealing engagement with the tissue and/or an inner coil.

Figure 2E:
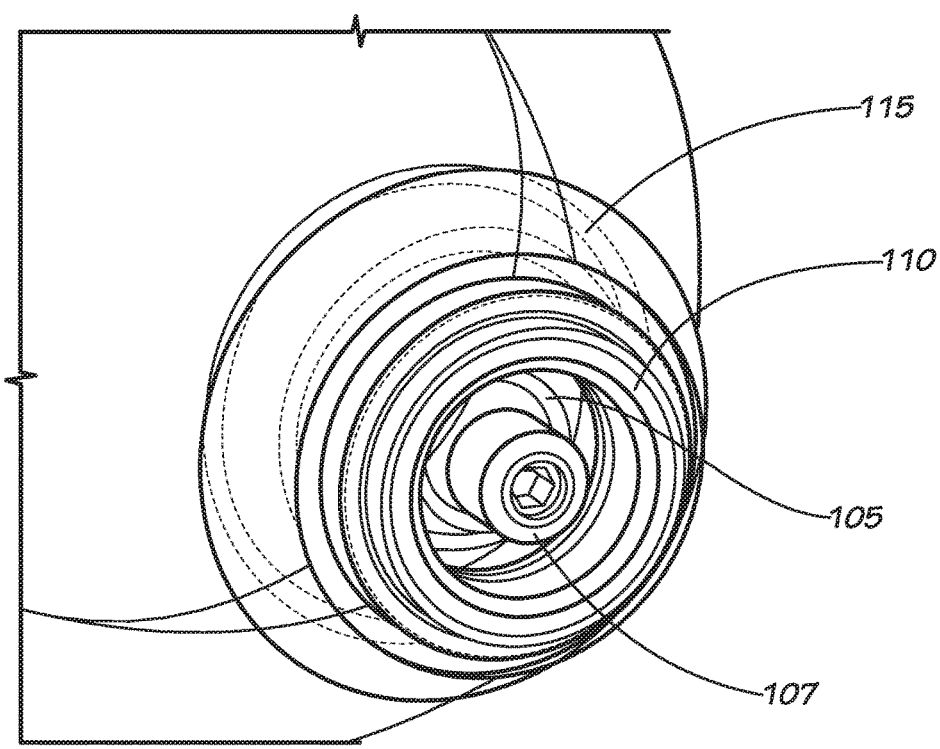

Additional details of embodiments of the coiled closure device 105 in sealed configuration through a tissue wall can be seen with reference to FIGS. 1, 2D, and 2E. According to one embodiment, the coiled closure device 105 further includes an engagement element 120 proximate the proximal end 107 of the coiled closure device 105. The engagement element 120 can be adapted to releasably receive a delivery instrument 130 to allow rotating the coiled closure device 105 during insertion into and removal from a tissue wall 300. In one embodiment, the engagement element 120 can be a substantially solid end piece that includes a receiving feature (e.g., the female or male element of a corresponding male/female instrument), such as, but not limited to, a straight slot, cross-shaped slot (e.g., for use with a phillips head), a hexagonal shape (e.g., for use with an allen head), or any other geometry or assembly that allows secure selective insertion of the head of a delivery instrument 130 therein. It is appreciated that, in other embodiments, a delivery instrument 130 may releasably secure to the engagement element 120 according to any other means, as desired. Moreover, in some embodiments, the delivery instrument 130 can be adapted for use with both the coiled closure device 105 and the outer coil 110, and both may include means for releasably receiving the delivery instrument 130.

FIG. 2A illustrates a perspective view of an outer coil 110 including a flange 115, in accordance with one embodiment of the invention. In the embodiment shown, the outer coil 110 includes a sharpened tip 205 at its distal end 114 adapted for piercing and easing insertion through a tissue wall. FIG. 2B likewise illustrates a perspective view of a coiled closure device 105 (inner coil), in accordance with one embodiment of the invention. The increasing radius of the coiled closure device 105 is clearly shown, increasing along the length of the coil from the proximal end 107 toward the distal end 109. It is appreciated that, while the coiled closure device 105 is shown as having a radius that increases along the entire length of the coil, in other embodiments, the radius may increase only along a portion of the length, such as at or near the distal end 109 (or at or near the proximal end 107), with the remaining length of the coil having a substantially constant radius. In this embodiment, the coiled closure device 105 also includes a sharpened tip 210 at its distal end 109 adapted for piercing and easing insertion through a tissue wall. Although an engagement element is not shown by FIG. 2B, it is appreciated that an engagement element may be included at or near the proximal end 107 of the coiled closure device 105 adapted for engaging a delivery instrument, such as is described with reference to FIG. 1 and FIG. 2E.

FIG. 2D illustrates another view of an outer coil 110 having a flange 115, to show one example perspective of relative dimensions compared to FIG. 2C, according to one embodiment. FIG. 2E illustrates a view of an outer coil 110 inserted through a tissue wall 300 and having a flange 115 positioned against the tissue wall. In FIG. 2E, the coiled closure device 105 is shown as being inserted through the approximate center of the outer coil 110 to close the tissue puncture site. In FIG. 2E, the difference in diameter between the outer coil 110 and the coiled closure device 105 shown at the proximal end 107 may be the contact site for the coiled closure device 105 flange 106. An engagement element 120 is shown at the proximal end 107 of the closure device 105.

The invention provides systems to prevent over or under insertion of the coiled closure device 105 including a visual based delivery instrument providing visualization of the puncture to visually detect when the tissue has been substantially sealed by the inner coil, such as by an at least partially transparent delivery instrument, endoscopic visualization, fluoroscopy, angiography, magnetic resonance imaging ("MRI"), or other visualization techniques.

Figure 3A:
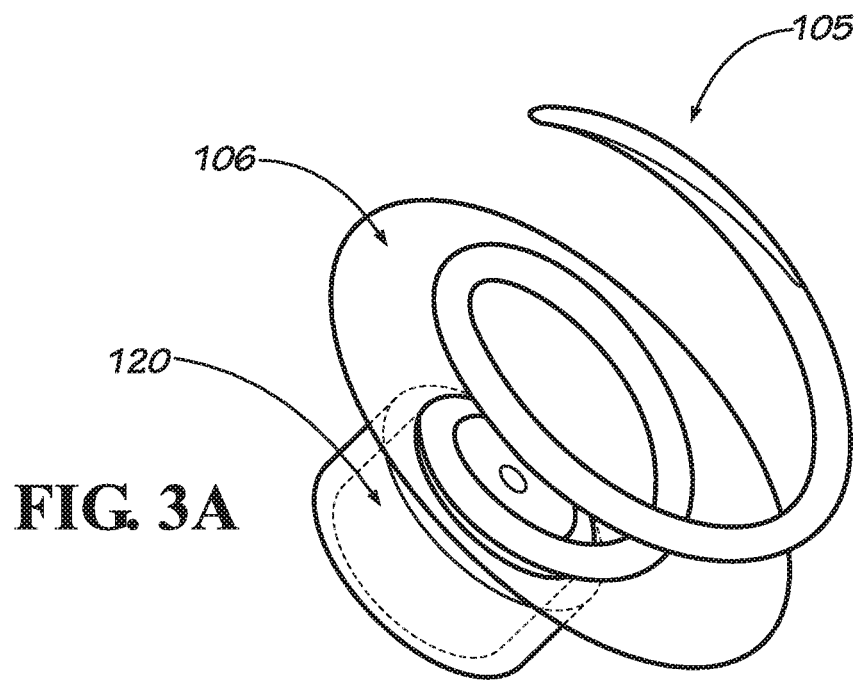
FIG. 3A-3H illustrate perspective views of various closure device depth indicator system embodiments of the present invention.
Figure 3B:
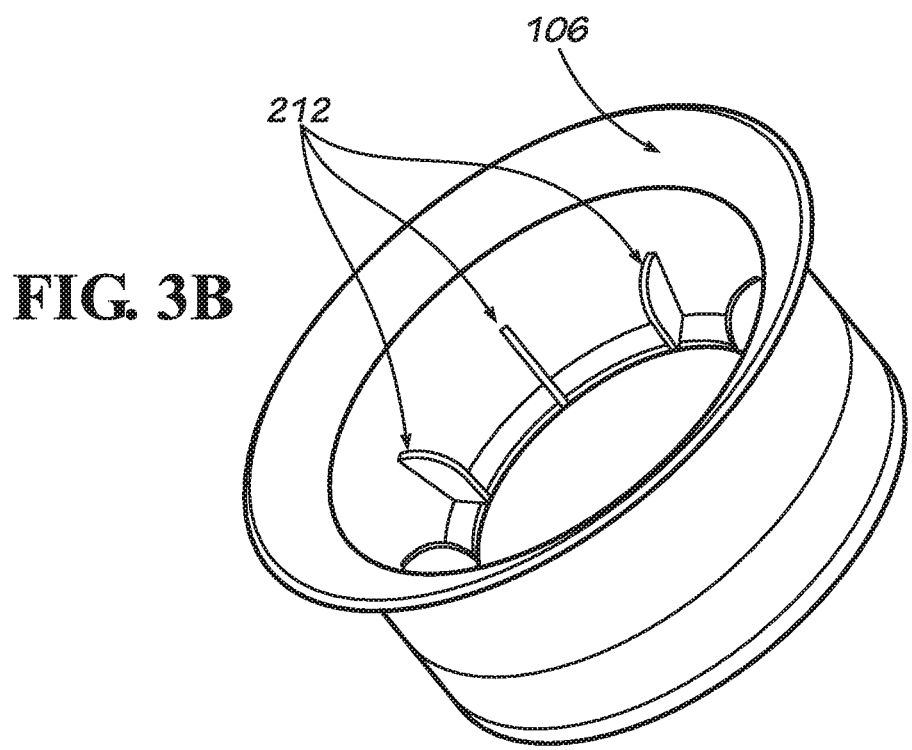

For example, the coiled closure device 105 may have a flange 106 or surface that may help in further sealing of the cut or puncture, as shown in FIG. 3A. This flange 106 may also help as a depth stop to control the penetration of the coil into the tissue. The flange 106 may be rigid, flexible or biodegradable or any combination of such material characteristics. The closure device of the present invention may include further systems for determining when the desired amount of tissue contact has been attained during delivery of the closure device. The flange 106, as detailed in FIG. 3B includes placement sensors 212 configured as wings extending therefrom to assist in determining when the desired amount of tissue contact has been attained during delivery. When properly seated against the tissue, sensors 212 will either provide mechanical resistance against the tissue detectable to an operator rotating the device, or the wings may be constructed of radio opaque materials and be deformable, such that upon contact with the tissue surface the placement sensors provide a visual marker for sufficient coil penetration. In alternative embodiments, electronic leads may be present as placement sensors on the flange which engage each other to complete a circuit when the flange is compressed against tissue to provide an electronic indication, such as a remote light indicator, of proper tissue engagement.

Figure 3C:
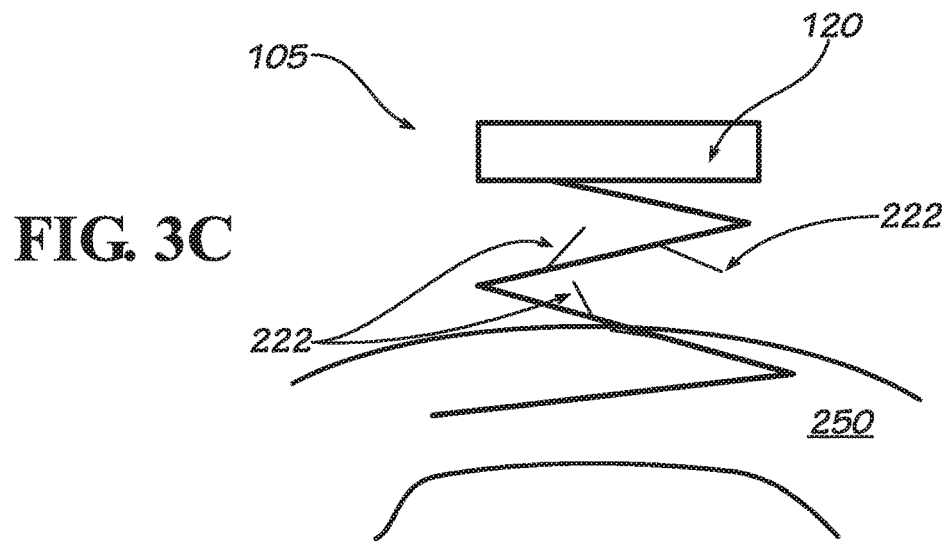

When delivering a closing element, such as a closure coil or a conduit securing coil, into a tissue surface, the level of tissue penetration is fundamental to its function. Therefore, the invention provides further systems for determining when the desired amount of tissue contact has been attained during delivery of the closure device. Such delivery depth indicator systems are primarily exemplified herein on coil embodiments, however, it is understood that these indicator features can be adapted for other closure device configurations. The tissue delivery depth indicators can be mechanical or electrical in operation. In one embodiment of the invention, a delivery depth indicator includes one or more deformable elements, which can be made radio opaque or fluoroscopic, extending from selected locations on the device. As shown in FIG. 3C, when one or more delivery depth indicator elements 222 extending from the surface of the coil delivery device 105 penetrate into the tissue 250, they become flattened against the coil surface, or otherwise deformed in geometry, such that the change is observable using well-known medical imaging techniques, and therefore can serve as a visual determination of the depth of coil penetration.

Figure 3D:
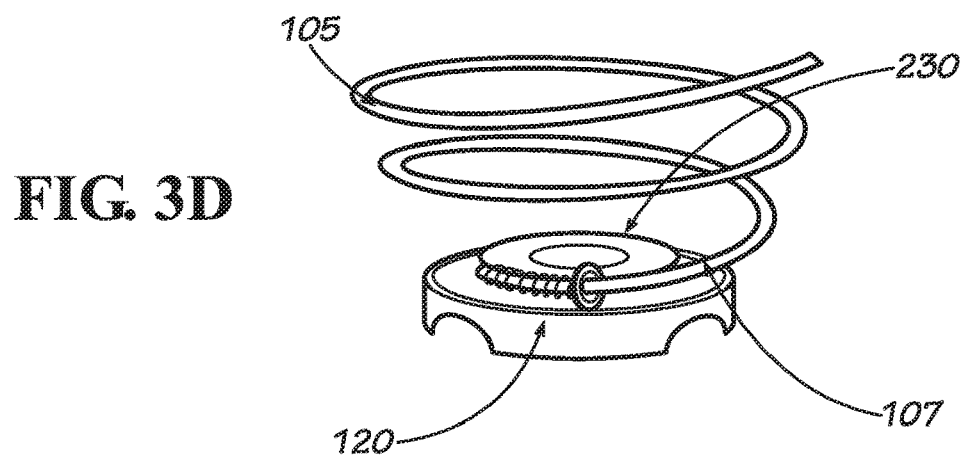
Figure 3E:
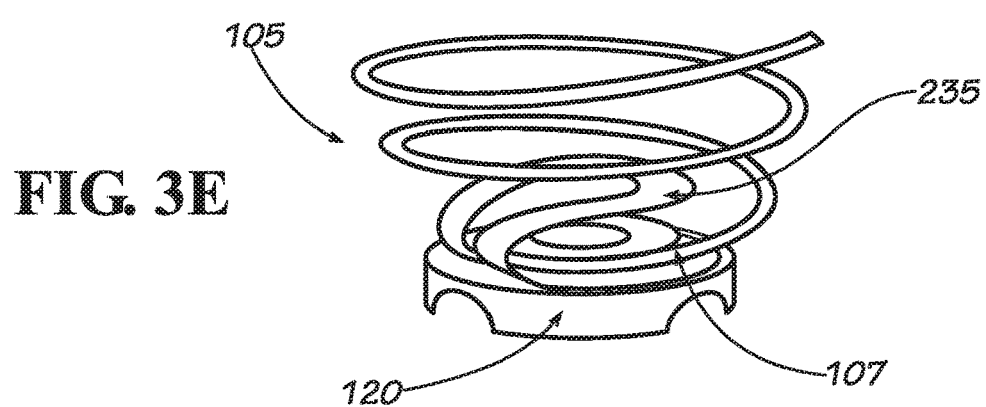

FIG. 3D illustrates an embodiment having a depth indicator element 230 adjacent to the proximal end 107 of the coil closure device 105. The indicator element 230 includes a spring coiled around the primary coil closure device 105 that will compress along the length thereof as the coil progresses into the tissue. The spring can be enclosed in a compressible polymer shield to protect the tissue from pinching in the compressing spring. FIG. 3E illustrates an embodiment having an alternative depth indicator element 235 configured as a deformable leaf adjacent the proximal end 107 of the coil closure device 105 and on the distal surface of the engagement element 120. The penetration depth indicator element 235 is a deformable leaf spring that will compress as the proximal portion of the coil progresses into the tissue.

In addition to the potential for visual confirmation of radio opaque or fluoroscopic material visible through medical imaging equipment, each of the deformable depth indicator elements provides increased mechanical tension against continued rotational insertion, which can be sensed manually by the operator, or mechanically by a torque sensitive delivery device, as described below with reference to FIGS. 5A-5D. The deformable depth indicator elements mentioned above may also serve as electrical switches, such that when the element or elements are deformed, an electrical circuit is opened or closed, activating a signal, such as a remote light indicator, corresponding to a predetermined coil depth. In an embodiment where the system is used in tissues that have intrinsic electrical signals themselves, such as the heart, a simple electrical sensor may be used adjacent the proximal end of the coil device, such that when in contact with such tissue the sensor will transmit using the conductivity of the tissue as an indicator of desired depth.

Figure 3F:
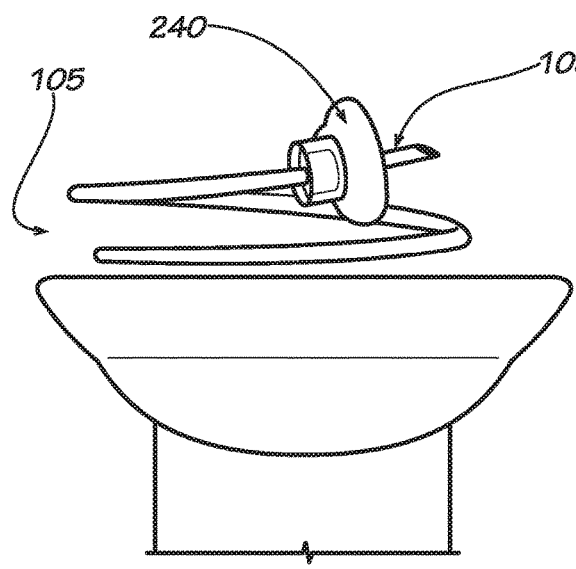

FIG. 3F shows another mechanically based depth indication element 240 provided by the invention which is slideably affixed to the distal end 109 of the coil of the closure device 105 such that the element 240 will travel proximally along the surface as the coil penetrates tissue due to mechanical contact of the element 240 with the tissue surface. Again, visualization of the position of such a tracker element 240 using radio opaque or fluoroscopic materials will allow for real-time visual assessment of penetration of the coil. This tracker element 240 may also activate a mechanical or electrical signal when it reaches a predetermined location or locations to provide a further indication of depth.

Figure 3G:
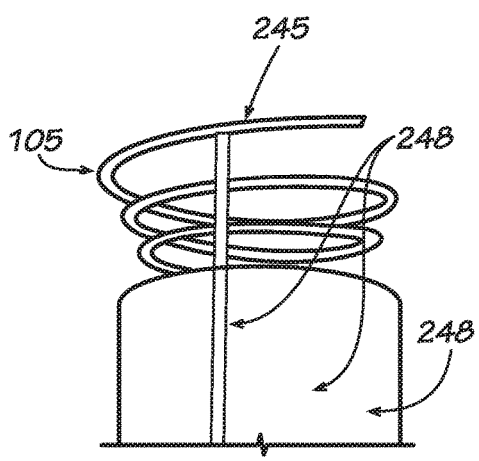
Figure 3H:
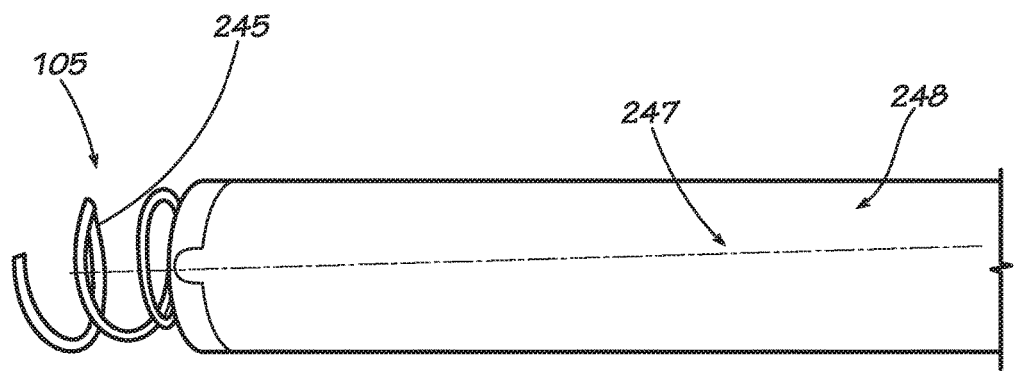

In yet a further embodiment as shown in FIGS. 3G and 3H, the depth indication element 245 is mechanically or electrically attached to an indicator support tool 247 on a delivery system which will show the relative position of the coil as it goes into the tissue. The depth indication element 245 can be a small coil slideably affixed to the distal end 109 of the coil of the closure device 105 such that the element 245 will glide proximally along the surface as the larger coil 105 is rotated into tissue. The indicator support tool 247 is attached to the depth indication element 245 and runs proximally parallel to the delivery instrument 248. As the delivery instrument 248 and coil closure device 105 are rotated, the indicator support tool 247 is held in place to prevent rotation, and thus element 245 will glide proximally along the surface of the coil 105 due to static contact with the restrained support tool 247. Proximal movement of the element 245 causes proximal movement of the indicator support tool 247, which can be measured in relative terms against the side of the delivery instrument 248, which can have predetermined marking thereon corresponding to designated tissue penetration depths, as shown in FIG. 3F. Removal of the depth indicator element 245 can be achieved by proximal pulling of the indicator support tool 247 to cause the small coil to unwind from the larger coil 105 for retraction from the surgical field.

In an alternative embodiment for a depth indicator, the delivery instrument for the coil of the closure device may have a central shaft attached to a proximal flange or collar of the device. The shaft may be positively or negatively pressurized, such that as the coil of the closure device goes into the tissue and the distal end of the shaft collar comes in contact with the tissue, the pressure or vacuum within the shaft will significantly change due to the seal against the tissue of such element. The change in pressure or suction may be used directly or through an indicator to signal complete apposition of the coil closure device against the tissue.

The invention further provides an embodiment with capability to electronically monitor and controllably stimulate the tissue. Therefore, the invention provides embodiments wherein the supporting member or the closing element comprises an electrode element capable of sensing an electronic signal from the tissue or delivering an electronic signal to the tissue. For example, the primary coil of the engaging device, or the smaller closure coil, embedded within cardiac tissue, can be connected by a lead wire or be in electronic wireless communication with a controller comprising an EKG monitor to detect arrhythmias in the heart, which in turn can be programmed to send a pacing electronic signal to the cardiac tissue through the coil to stimulate proper heart beating, as well as to send a signal notifying a designated physician. Different conductive elements of the implanted devices may also be electrically isolated between them to allow for connection of multiple leads. The lead and/or leads may selectively disengage from the implant when the delivery tool is retrieved or remain in the body as part of the implant for a long or short term in order to facilitate monitoring or stimulation of the tissue during patient treatment.

It is appreciated that the various device components described herein may comprise a variety of biocompatible materials including, but not limited to, biocompatible metals or metal alloys, such as stainless steel or titanium; substantially rigid biocompatible polymers; elastomeric biocompatible polymers; biodegradable polymers, or various combinations of such materials. For example, in some embodiments, the coiled closure device 105 and/or the outer coil 110 (or other closure device members, such as pins, arms, etc.) may comprise a biocompatible metal, a metal alloy, and/or a substantially rigid biocompatible polymer, or a combination thereof. In some embodiments, other aspects of the coiled closure device 105 and/or the outer coil 110, such as the flange 115 of the outer coil or the engagement element 120 of the coiled closure device 105, may comprise substantially rigid biocompatible polymers and/or a biocompatible metal, metal alloy, or a combination thereof.

In one example, the outer coil 110 may be formed from a biocompatible metal and/or metal alloy that is embedded substantially within and/or operably engaged with an injection-molded polymer used to form the flange 115. For example, as shown generally in FIGS. 1 and 2A-2B, the outer coil 110 may be integrally formed within the flange 115, such as by being placed at least partially in a mold such that the polymeric or other components of the flange 115 may be molded substantially around at least a portion of the outer coil 110. In other embodiments, the outer coil 110 may be operably engaged with at least a portion of the flange 115 according to a number of other techniques, such as, but not limited to, by adhesive, RF welding, mechanically securing (e.g., threaded, friction fit, snap fit, etc.), and/or other suitable attachment methods.

The coiled closure device 105 and its engagement element 120 may likewise be formed from the same or similar materials and in a same or similar manner as described with reference to the outer coil 110. In some embodiments of the device all or some components of the outer coil 110 and coiled closure device 105 may be made of biodegradable materials. It can be advantageous when the penetrating element or surface contact element of these components is made of biodegradable materials in order to prevent long term migration and to allow for re-access. Similarly, the flanges 115, 106 of the outer coil 110 or coiled closure device 105 may hold some biocompatible adhesives, not limited to but including fibrin glue, or expandable agents such as collagen, on their inner surface to improve sealing and positioning onto the tissue wall.

Figure 4A:
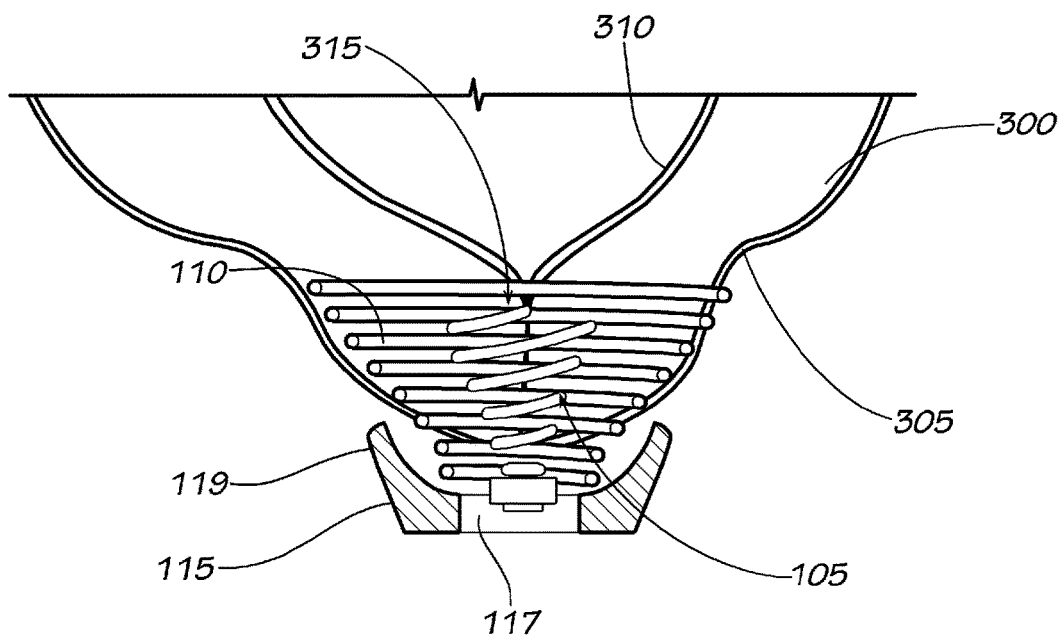
FIG. 4A illustrates a cross-sectional view of an outer coil and a coiled closure device positioned within the outer coil and both implanted within a tissue wall, in accordance with one embodiment of the invention

FIG. 4A illustrates a cross-sectional view of an outer coil and a coiled closure device positioned within the outer coil and both implanted within a tissue wall, in accordance with one embodiment of the invention. As shown by FIG. 4A, an outer coil 110, such as is described with reference to FIGS. 1 and 2A, can be inserted at least partially into a tissue wall 300. The tissue wall 300 is illustrated has having a first surface 305 (e.g., an outer surface) and a second surface 310 (e.g., an inner surface). Similarly, the coiled closure device 105 (inner coil) can also be rotatably inserted through the tissue wall 300, closing a previously formed puncture 315 by the inward compress caused by the increasing radius of the coiled closure device 105.

According to one example embodiment using a coiled closure device, the outer coil 110 may be inserted into the tissue wall 300 to initially secure a conduit device (not shown, such as if already removed) extending through the tissue wall 300 by compressing the tissue wall 300 inward against the conduit and creating a substantial seal therewith. For example, after inserting the outer coil 110 at least partially through the tissue wall 300 (inserting from the first surface 305), a coring device may be passed through the approximate center of the outer coil 110 to puncture the tissue wall 300 and optionally remove a portion thereof. After defining the puncture 315 (already shown in FIG. 4A in a closed state) through the tissue wall 300, a conduit may be inserted therethrough, providing fluid communication between the first surface 305 and the second surface 310 of the tissue wall 300 (e.g., into a ventricle if the tissue wall 300 represents a cardiac apex, etc.).

Figure 4B:
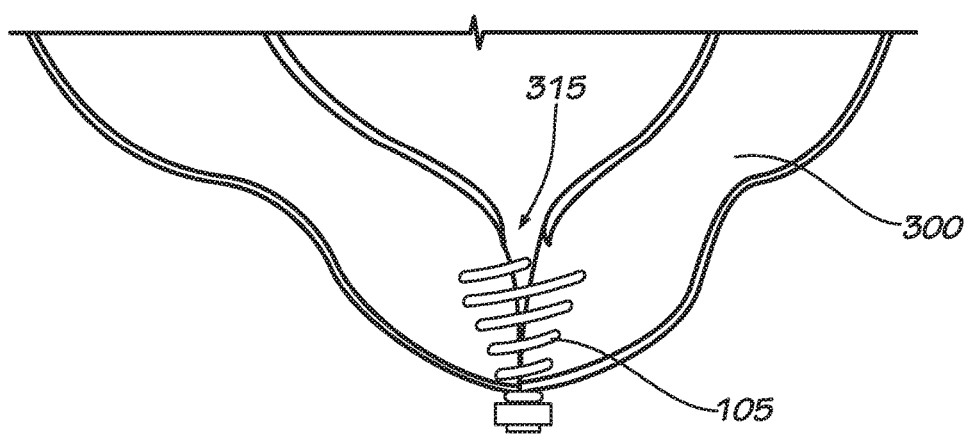
FIG. 4B illustrates a cross-sectional view of a coiled closure device positioned within a tissue wall, in accordance with one embodiment of the invention.

As described above, the increasing radius of the outer coil 110 will compress the tissue of the tissue wall 300 inwardly to seal against the conduit. Upon removing the conduit, which may be performed during and/or after the corresponding surgical procedure, the coiled closure device 105 may be rotatably inserted through the approximate center of the outer coil 110 (through the opening 117 of the flange 115) and at least partially through the tissue wall 300, surrounding the puncture 315 created in the tissue wall 300. The increasing radius of the coiled closure device 105, in combination with its reduced coil diameters relative to the outer coil 110, allow the coiled closure device 105 to further compress the tissue wall to substantially close the puncture 315, minimizing or eliminating fluid flow therethrough. In some circumstances, the outer coil 110 may be removed, leaving the coiled closure device 105 within the tissue wall 300 and substantially sealing the puncture 315, such as is shown by FIG. 4B.

Therefore, the coiled closure device 105 is shown in FIG. 4A having been inserted for closing a tissue wall 300 with the accompanied use of an outer coil 110. However, in other embodiments, the coiled closure device 105 may be utilized separately without the prior use of an outer coil 110 or after an outer coil 110 (or other supporting element) has been removed. FIG. 4B, therefore, illustrates a cross-sectional view of a coiled closure device 105 positioned within a tissue wall 105 without the presence of an outer coil, having substantially closed a tissue puncture 315.

Figure 7A:
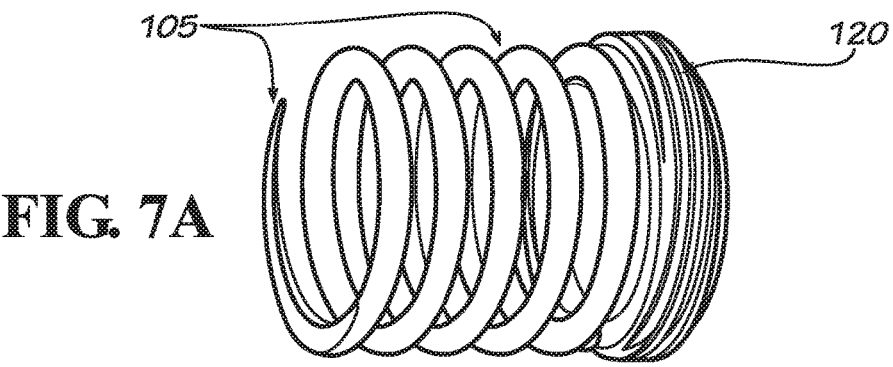
FIGS. 7A-7B illustrate perspective views of example closure devices, in accordance with various embodiments of the invention.
Figure 7B:
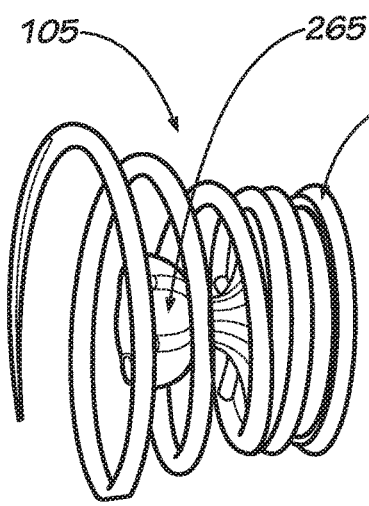

The invention provides many alternative configurations for a coil closure device such as follows. FIG. 7A shows an alternative embodiment for closure device 105 having a plug (or cap) as the engaging element 120 for occluding the attaching device orifice also having a threaded exterior surface for engaging corresponding threads on the interior orifice of the attaching device, and further having a distal end 109 coil disposed thereon, smaller in diameter than the coil on the attaching device into which it is inserted, creating a coil-within-a-coil sealing effect. This inner coil on the plug rotatably engages tissues within the orifice, drawing the tissues together in a sealing conformation. FIG. 7B shows an alternative embodiment of a closure device 105 having a plug (or cap) as the engaging element 120 for occluding the attaching device orifice having a radially expanding distal coil disposed thereon, smaller in diameter than the coil on the attaching device into which it is inserted.

The invention contemplates any shape of the inner coil closure device 105 suitable for rotational insertion, including a radially expanding cone-shape, inverted cone-shape, oval, hour-glass or pear-shape, for example. In the embodiment shown in FIG. 7B, the engagement element 120 base is not threaded, but rather engages the attaching device through corresponding ridges on the interior orifice of the attaching device. The invention contemplates any engagement mechanism for interlocking the plug of the closure device and attaching device, such as threads, expandable bearings snaps, bayonet clips, or a locking outer collar, for example. The plug with a sealing coil can be constructed of any suitable materials, including biodegradable polymers or metal alloys containing for example magnesium, and can be surface textured, or coated or impregnated with any bioactive agents, as described above.

In certain embodiments, the plug can be configured with a re-accessible valve for re-entry through the tissue wall. As shown in FIG. 7B, the plug of the engagement element 120 can be configured with a collapsible one-way occluding element 265, such that the seal is made more secure by pressure against the distal side when implanted, but that will yield to pressure from the opposite side. Therefore, the closure device can be configured for complete removal for re-access, or configured as a one-way valve or a diaphragm for limited re-entry and resealing. In addition, the invention provides for the use of biocompatible polymeric surfaces to facilitate ingrowth of tissues, such as DACRON, disposed in a ring pattern on those aspects of the attaching device in contact with the proximal (outer) tissue surface, particularly on the outer sealing ring, or extending body of the flange of the attaching device.

The closure device and engaging element of the present invention can provide a further sealing transmural compressive force across the tissue wall when in position. Thus, in addition to the radially compressive forces provided by the primary outer coil on the tissue against the walls of the conduit, the invention also provides a transmural compression via the occlusive plugs between the attaching device, particularly the outer sealing ring of the attaching device, and the proximal tissue surface. The combination of compressive forces provides a secure post-surgical environment. The occlusive plug valve 265 may also have a cone or hour-glass shape as shown in FIG. 7B, where fluid pressure can hold the occluding plug secure by deforming the distal end radially outwards, providing additional transmural sealing forces against the tissue wall.

Figure 8A:
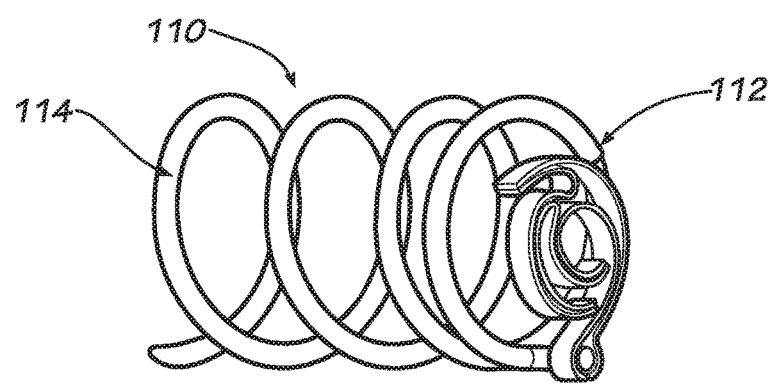
FIGS. 8A-8C illustrates a perspective view of an outer coil in various stages of expansion of one embodiment of the invention.
Figure 8B:
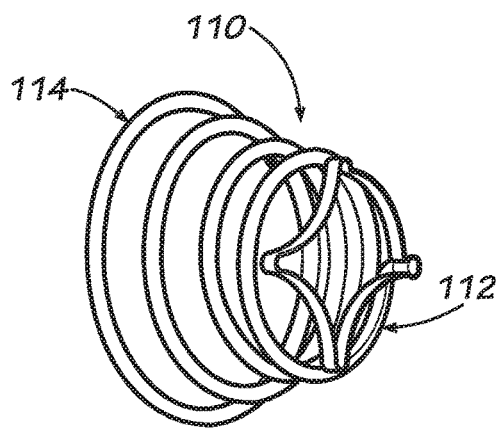
Figure 8C:
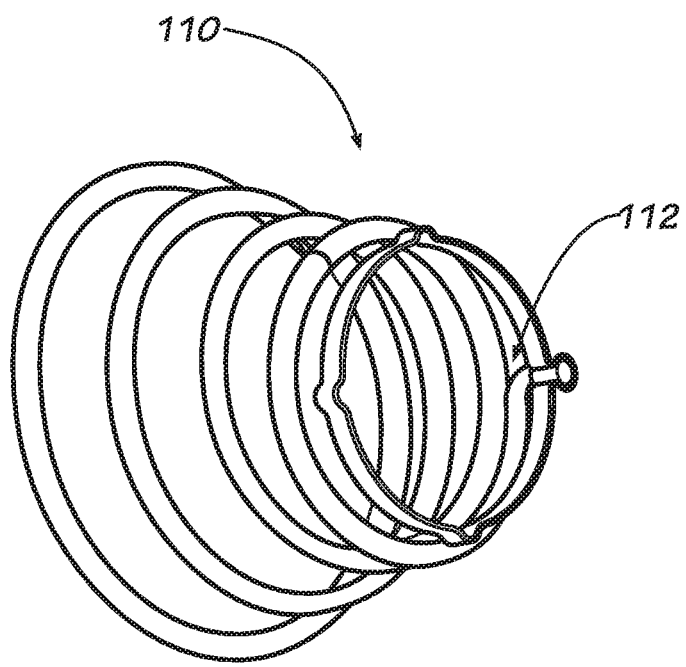

Other embodiments of the invention are designed for minimally invasive, endovascular or transcutaneous delivery. Any of the various expanding members described herein may be configured to expand and/or collapse using one or more of: mechanical actuation, material properties, structural properties, electrical excitation, thermal excitation, and/or any combination thereof. FIGS. 8A-8C illustrate perspective views of an example collapsible attaching device system for endovascular percutaneous delivery, shown in a collapsed, partially expanded and expanded state provided by the invention. In such embodiments, the attaching device including the coil 110 can be made of a shape memory polymer or alloy which has a collapsible geometry for delivery within a minimally invasive catheter. The coil in FIG. 8A is tightly wound for delivery and configured as a helix, which expands radially upon unwinding such as when the coil is proximally exposed for delivery from a catheter. In FIGS. 8B and 8C the coil and attachment device is successively unwound, particularly more so at the distal end 114, for use in situ in a surgical procedure. As shown in FIG. 8C, the proximal end 112 can also expand for engagement with the closure device in situ.

In embodiments using sharpened coils as attachment devices or closure devices, the coils may be protected within a sheath, sleeve or shaft, so that the sharpen of the coil does not undesirably catch against surgical elements or tissue when being delivered. In an embodiment wherein the sharpened coil is protected during delivery, the sheath can be selectively retracted proximally to expose the sharpened tip. The sheathed embodiment also facilitates compaction of the expandable members during endovascular or percutaneous delivery, as described above with respect to FIG. 8. During the procedure, such as after the sharpened end of the coil has been inserted into tissue, the sheath may be more fully retracted to allow access and visualization of the coil delivery to the desired depth.

FIGS. 5A-5D illustrate various features of example delivery instruments used with the present invention. The delivery of the coiled closure device 105 may be performed with the use of a delivery instrument 130 adapted to releasably engage the coiled closure device 105 and impart rotational force to the coiled closure device 105. In some embodiments, the delivery instrument 130 may include a mechanism adapted to prevent over insertion and/or under insertion of the coiled closure device 105. An example delivery instrument 130 having a proximal end 510 and a distal end 505 that includes an attachment mechanism 120 for releasably attaching to the coiled closure device 105, according to one embodiment. The delivery instrument of this embodiment includes a hollow shaft 515 between the proximal end 510 and the distal end 505, having a passage defined therethrough. At the proximal end 510 of the delivery instrument 130, a handle member 530 includes a release mechanism 525. The release mechanism 525 may be in operable communication with the attachment mechanism 120 at the distal end of the delivery instrument 130, such as by a shaft member 520 extending therebetween through the passage of the hollow shaft 515.

According to one embodiment, the release mechanism may be a torque-based release mechanism that will cause release of the delivery instrument from the coiled closure device upon achieving a selected torque or resistance imparted upon the rotation of the coil through the tissue. Resistance may be generated when the flange or a delivery depth indicator element (or other proximal aspect) of the coiled closure device reaches the tissue wall causing greater resistance on the turning coil. Conventional torque-based release mechanisms, such as, but not limited to, those similar to that utilized with manual torque wrenches, may be utilized with a selective releasing mechanism to release the delivery instrument from the coiled closure device.

Figure 5A:
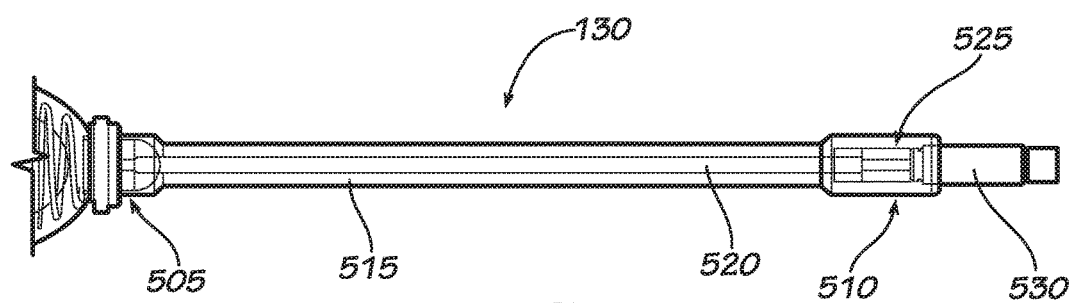
FIGS. 5A-5D illustrate perspective views of delivery instruments, in accordance with various embodiments of the invention.
Figure 5B:
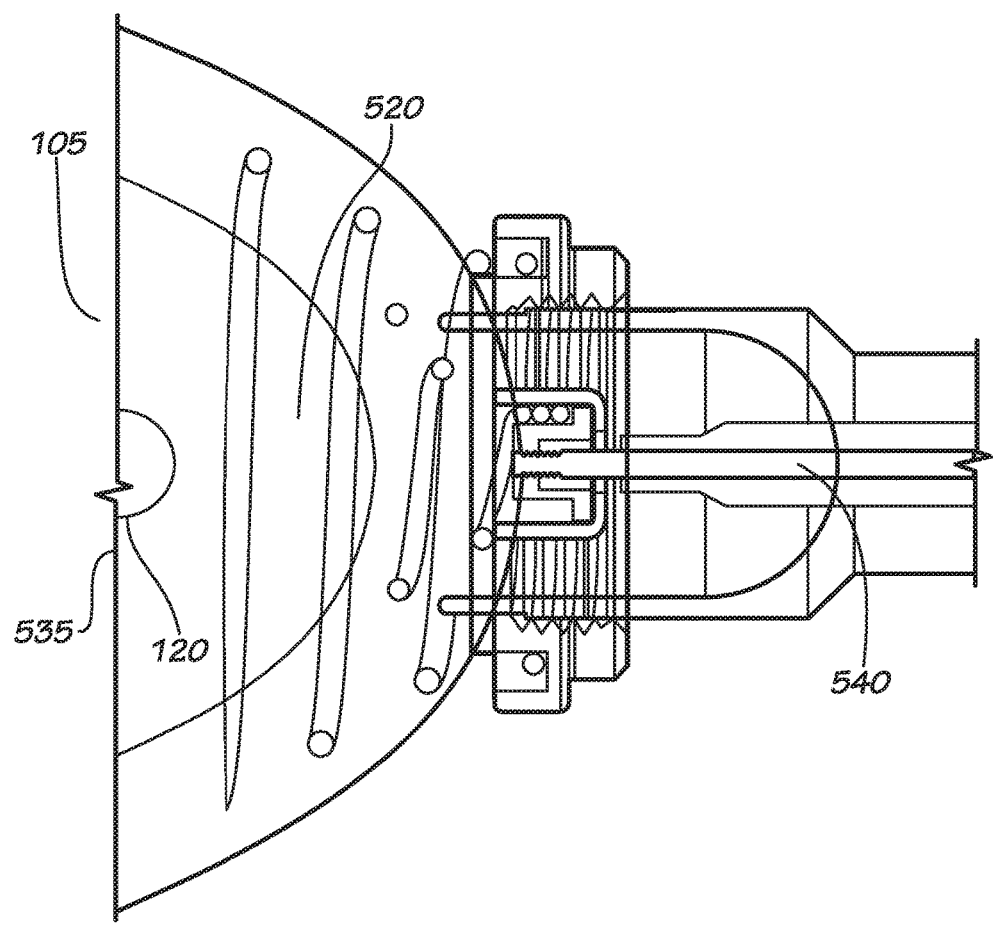
Figure 5C:
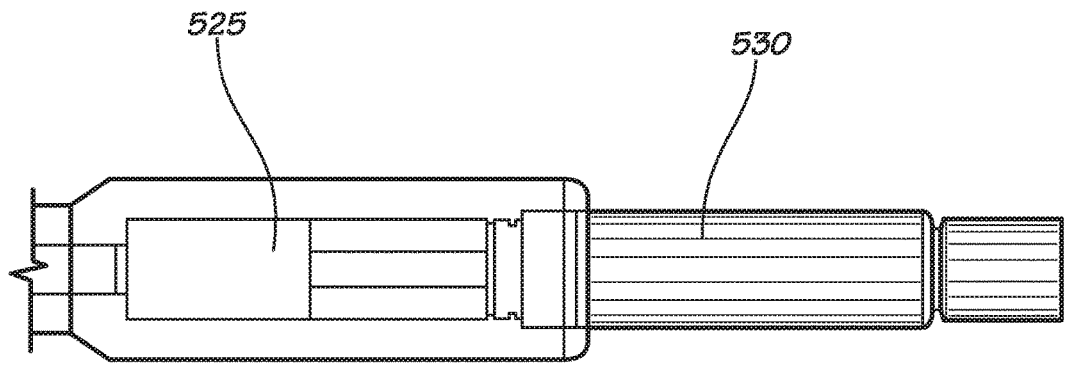
Figure 5D:
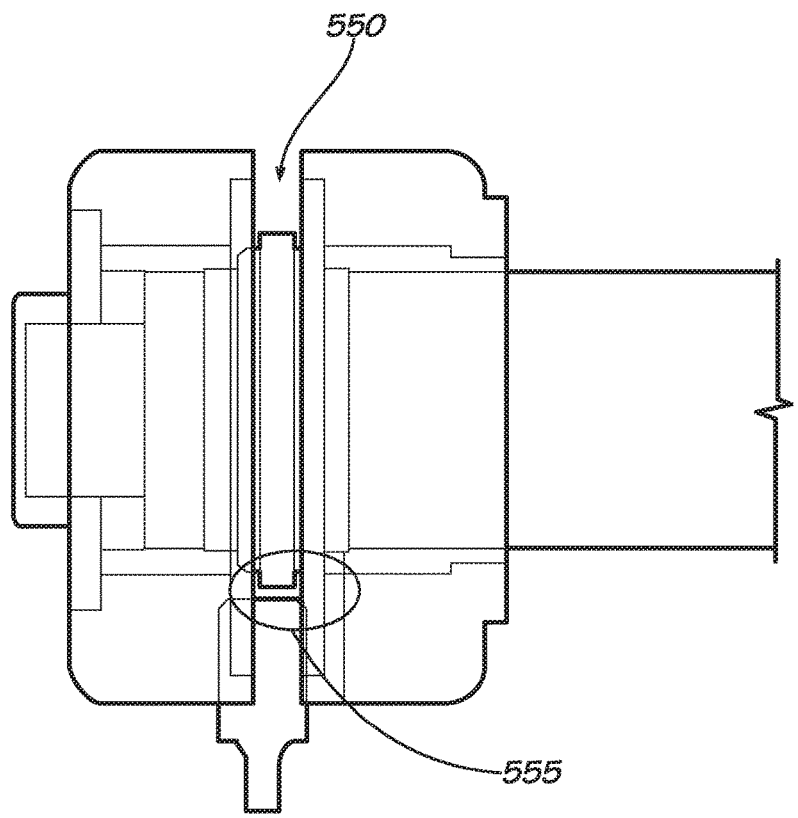

FIGS. 5C-5D illustrate different views of a release mechanism 525, according to one embodiment. As shown in FIGS. 5C and 5D, the handle member 530 may be in selectively rotatable communication with the release mechanism 525. A torque-based release mechanism 525 may, in one embodiment as shown in FIG. 5D, generally include a ratchet mechanism having a round (or linear) gear track 550 and pawl 555 (or other member) operable to releasably engage the gear track 550, allowing the operator to manually disengage the pawl 555 from the gear track 550, such as is known. According to various other embodiments, the release mechanism may further include a torque display means or an automatic torque release means, which displays a measurement of torque achieved and/or releases the attachment mechanism and/or the release mechanism from operating when a predetermined amount of torque is reached. Alternatively, the torque release mechanism may operated by disengagement of the handle member when the coiled closure device has extended at least a predetermined distance away from the distal end.

Another example technique to prevent over or under insertion may include a displacement-based delivery instrument that is calibrated based on certain dimensions of the coil, such as the coil length, the number of turns, the radiuses, the length of the coil from its proximal end to its distal end, and/or any combination thereof, or any other useful dimensions, to determine full insertion of the coil into the tissue wall and to allow release upon full insertion. For example, a displacement mechanism may include a gauge member that visually displays the progress (e.g., the number of coils, remaining length, a moving status element, etc.) based on mechanical displacement resulting from the turning of the coils. The gauge member may be seen by an operator for determining when full insertion has been achieved.

A further example of a displacement-based mechanism to prevent over or under insertion is the use of a calibrated thread in the delivery instrument so that elements of the delivery instrument, such as but not limited to, a handle will advance as the coil goes into the tissue until a predetermined stop on the delivery instrument. When that stop is reached the motion of the coil is restricted by mechanical interference of elements on the delivery device. An important aspect of such a system is that the pitch of the coil would be similar or the same as the pitch of the coil so that the elements in the delivery system advance at the same rate of the coil preventing tearing of the tissue. In a further embodiments, the stop for a displacement-based mechanism may be movable to allow for different levels of penetration of the same coil at controlled locations. The stop of the handle can be attached to a cam based button which when activated removes the stop from the path of the handle of the delivery device and therefore allows for further displacement of the coil relative to the tissue.

Figure 6A:
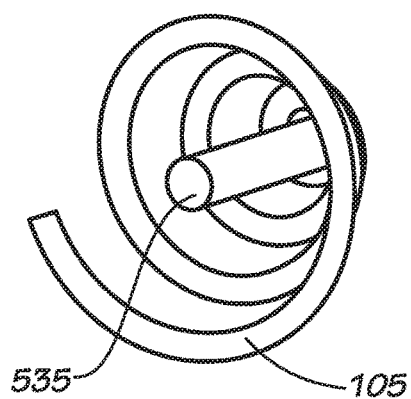
FIGS. 6A-6D illustrate perspective views of example outer coils and/or coiled closure devices, in accordance with various embodiments of the invention.
Figure 6B:
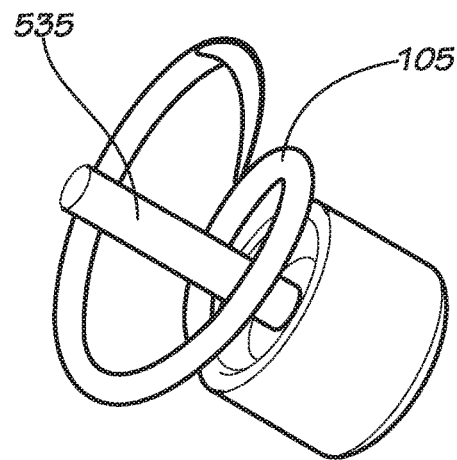

FIGS. 6A-6D illustrate other aspects of exemplary closure devices, which includes a centering member 535 extending distally at least partially through the approximate center of the coiled closure device 105, which will allow centering the coiled closure device 105 within the puncture site of the tissue to be closed. Centering the coiled closure device 105 within the puncture site will cause equal distribution of the coil through the tissue and thus improve the purchase of the coil within the tissue when urging it inward. The shaft member 520 of the delivery instrument may also be hollow and insertable over a separate guide wire with the centering member 535 capable of receiving the guide wire therein at its distal end. According to another embodiment, however, a centering member 535 may be integrated with the coiled closure device 105, such that it will extend through the tissue puncture when screwing the coil therethrough, as shown in FIG. 6B. In this example, a guide wire and centering member 535 combination may not be required for centered insertion of the coiled closure device 105; though, it may optionally be utilized in addition (e.g., such as if the centering member 535 of FIG. 6B is also hollow).

Figure 6C:
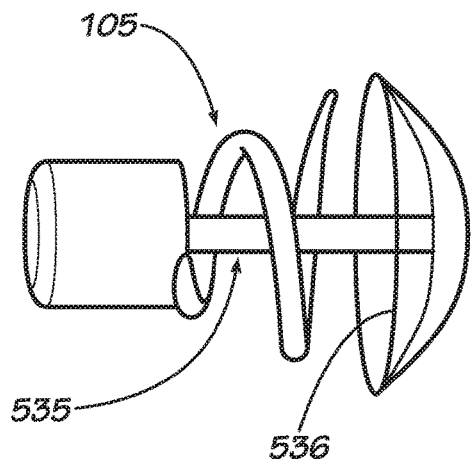
Figure 6D:
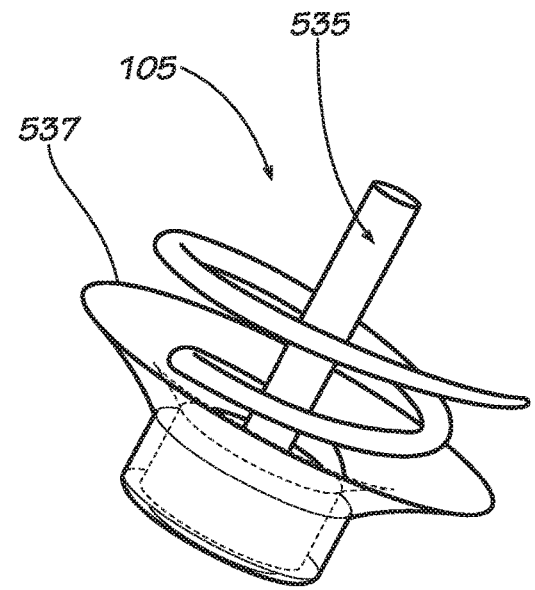

The centering member 535 may also serve as a sealing surface or plug for the tissue which is compressed inward by the coiled closure device 105. As shown in FIGS. 6C and 6D, the centering member may also hold a flange or umbrella-shaped component near or on its distal end 536. The flange or umbrella component may be flexible or rigid but should allow for penetration into the tissue through the puncture site while the coil is being advanced. The flange 536 or umbrella type device will provide further sealing when in contact with the inner surface of the tissue wall. Inner and outer flange elements 536, 537 by themselves or in conjunction may be used to provide further sealing for the coiled closure device as illustrated in FIGS. 6C and 6D.

FIGS. 9A-9G illustrate cross-sectional views of additional embodiments of a closure device, including an inner coil and an outer coil and/or flange. The outer coils and/or flanges can be utilized to provide support to a tissue wall to prevent further expansion and/or tearing of a tissue puncture, in accordance with various embodiments of the invention.

Figure 9A:
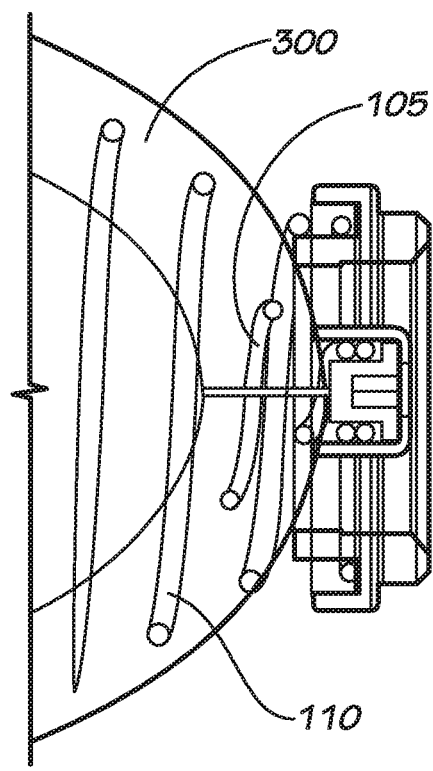
FIGS. 9A-9G illustrate cross-sectional views of various coil-in-coil embodiments for the present invention.
Figure 9B:
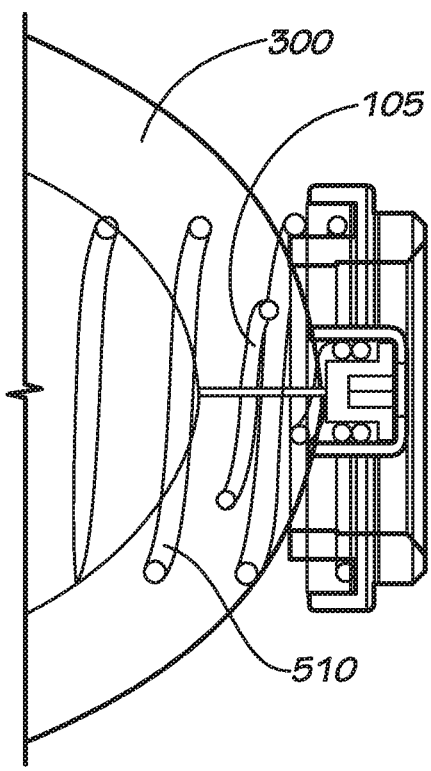

FIG. 9A illustrates an outer coil 110 and a coiled closure device 105, both having an increasing radius, such as is also illustrated and described with reference to FIGS. 1-3. FIG. 9B illustrates an outer coil 510 having a substantially constant radius, in contrast to the increasing radius coil, according to one embodiment. In this embodiment, the coiled closure device 105 still has an increasing radius. In this embodiment, the radius of the outer coil 510 is substantially constant along the length of the coil, and thus, the outer coil 510 will exert significantly less inward compressive force. However, the multiple outer coil 510 segments passing through and positioned with the tissue wall serve to support the tissue and prevent further expansion or tearing.

Figure 9C:
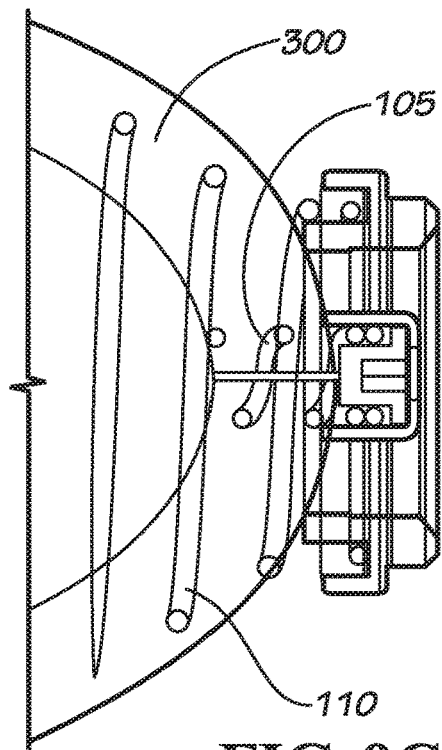
Figure 9D:
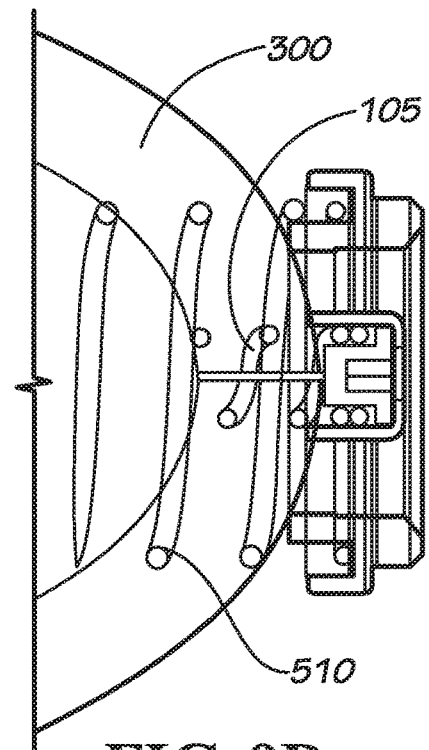

FIG. 9C illustrates an embodiment having an outer coil 110 with an increasing radius, and a coiled closure device 505 having a substantially constant radius, according to one embodiment. FIG. 9D illustrates the combination of an outer coil 510 and an inner coil 505, both having a substantially constant radius, according to another embodiment. Closing inner coils having a substantially constant radius will still create radially inward sealing compression on the tissue puncture, because the inner coil occupies a portion of the tissue volume already defined by the insertion of the outer stabilizing coil.

Figure 9E:
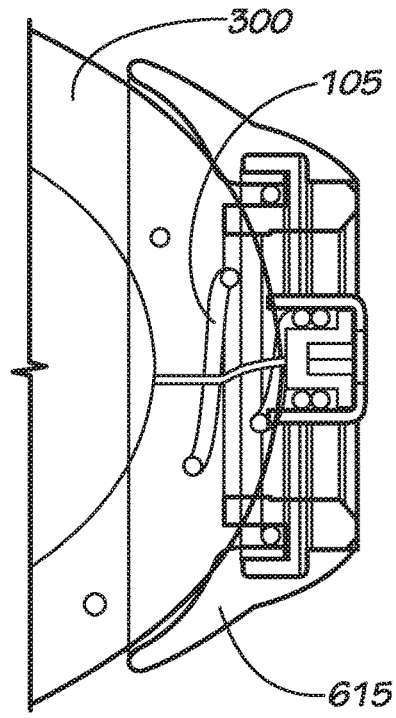
Figure 9F:
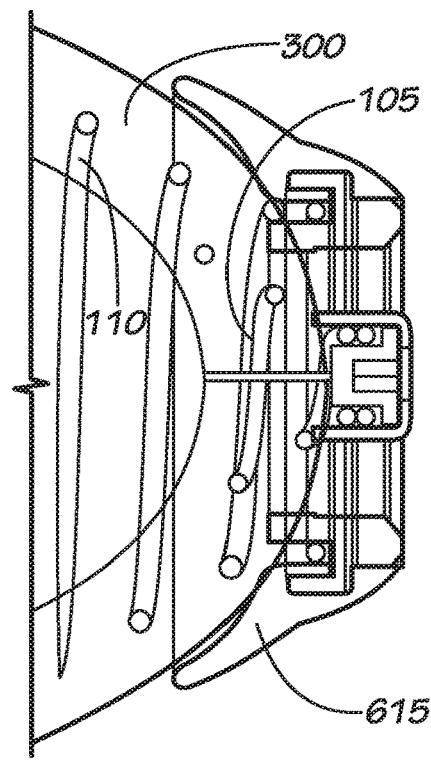
Figure 9G:
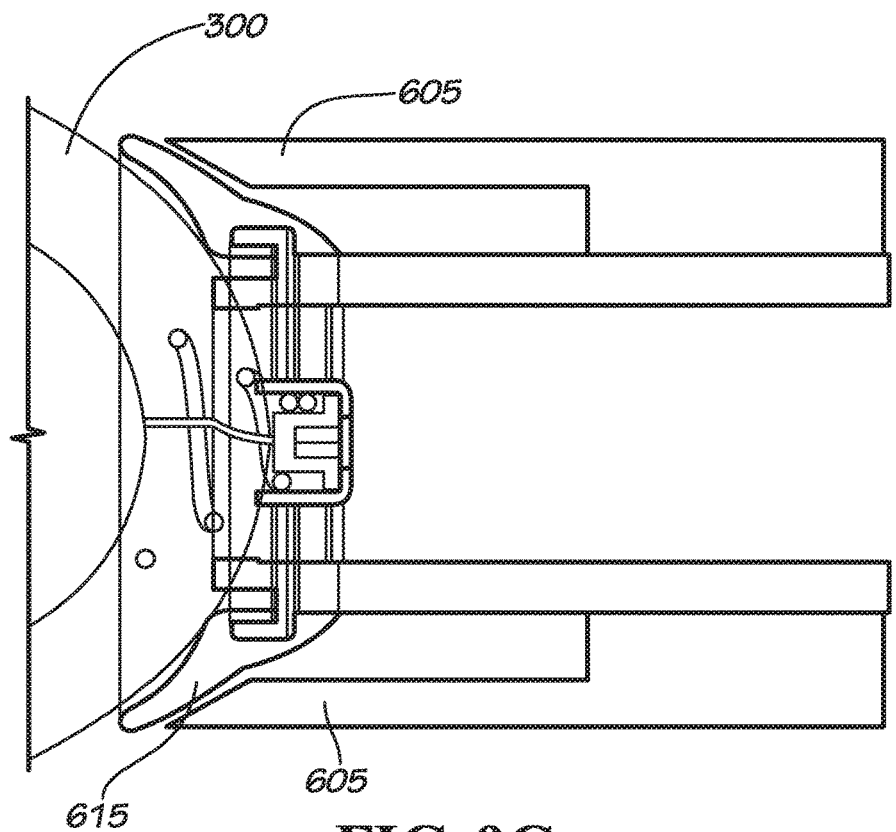

According to one embodiment, as shown in FIG. 9E, a closure device may include a flange 615, which may be similar the flange 115 described with reference to FIG. 1. This flange, however may be affixed to the coiled closure device 105 and utilized to cause an inward force, urging the tissue at or near the puncture side inward. According to one embodiment, the flange 615 may cause a suctioning force against the tissue wall, which further facilitates securing the tissue wall and/or urging the tissue wall inward. FIG. 9F illustrates another embodiment, in which the closure device includes both an inner coil 105 and an outer coil 110, as well as a flange 615. FIG. 9G illustrates a partial view of a distal end of a delivery instrument to be utilized with a closure device including a flange 615, which has outer members 605 adapted to compress at least a portion of the flange 615 and improve the sealing force against the tissue wall. It is appreciated that a flange, such as the flange 615 described with reference to FIGS. 9E-9G may be utilized with any of the other closure device embodiments described herein, and is not limited to the configuration combinations shown in FIGS. 9E-9G. It is further appreciated that the coils and flanges described with reference to FIGS. 9A-9G may be formed from materials and in manners similar to that described herein with reference to the supporting outer coil 110 and the closing coil 105, previously described. Moreover, the supporting elements or closing elements of all of the embodiments can be constructed of a shape memory material, such as nitinol, which can further be designed to selectively expand and retract in response to operator stimulation, such as an electric current or temperature.

FIGS. 10A-10J illustrate yet additional embodiments of closure devices having supporting elements that support and/or urge tissue inward, which may not include outer coils. According to these embodiments, instead of a radially expanding coil, other apparatus can be utilized to be inserted at least partially into a tissue wall and/or at secured to one or more surfaces of the tissue wall to prevent further expansion of the tissue wall. Such apparatus may be beneficial with tissues that are prone to tearing (e.g., cardiac tissue, etc.), that may otherwise result in an undesirable increase in puncture size either during the surgical procedure or during or after attempting to close the puncture.

Figure 10A:
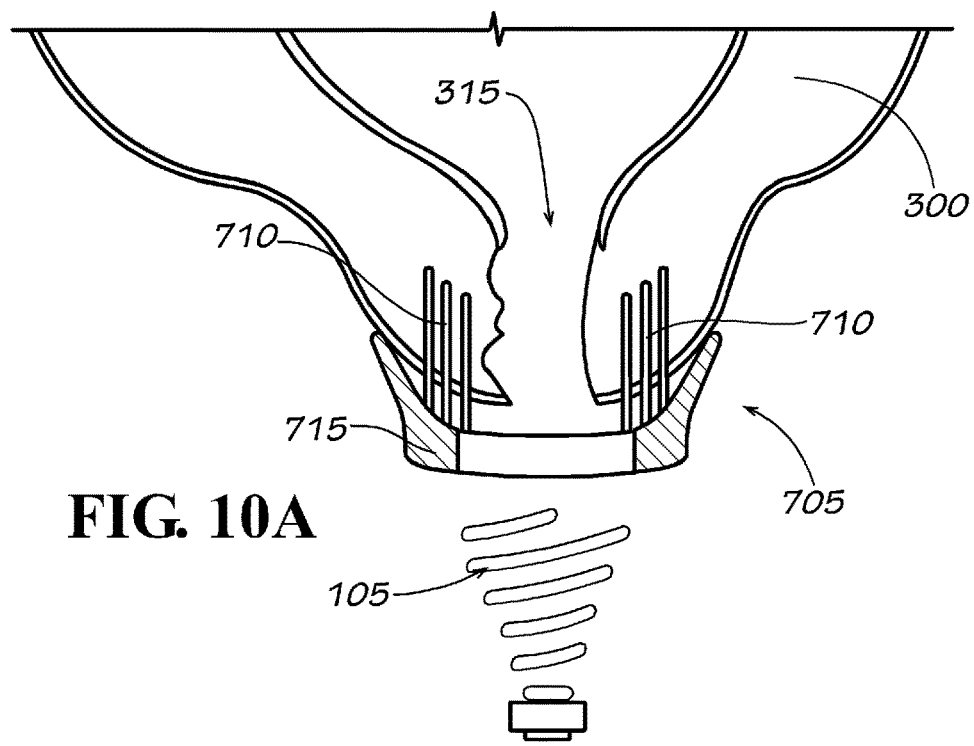

For example, FIG. 10A generally illustrates a pinned supporting element 705 including multiple straight pins or needle members 710 extending from a flange 715 and adapted for insertion at least partially through a tissue wall 300 to prevent further tearing or expansion of a puncture 315, according to one embodiment. In this embodiment, instead of a coil being rotatably inserted into a tissue wall 300, the pins or needle members 710 may be pushed straight into and at least partially through the tissue wall 300, providing support to the tissue wall 300. According to one embodiment, the pins or needle members 710 may have a sharpened distal end. In one embodiment, the pins or needle members 710 may extend from the flange 715 in a radially spaced apart pattern, forming a circular or semi-circular pattern that will encircle a tissue puncture 315 site. However, in other embodiments, other configurations may be utilized, such as according to the example embodiments illustrated and described with reference to FIGS. 10B-10G. Similar to that described with reference to FIGS. 1-4, a coiled closure device 105 may be inserted through the center opening of the flange 715 and into the tissue wall 300 to compress the tissue and substantially close the puncture 315.

It is appreciated that the pinned supporting element 705 and flange 715 may be formed from materials and in manners similar to that described herein with reference to the outer coil 110 and/or the coiled closure device 105.

Figures 10B, 10C:
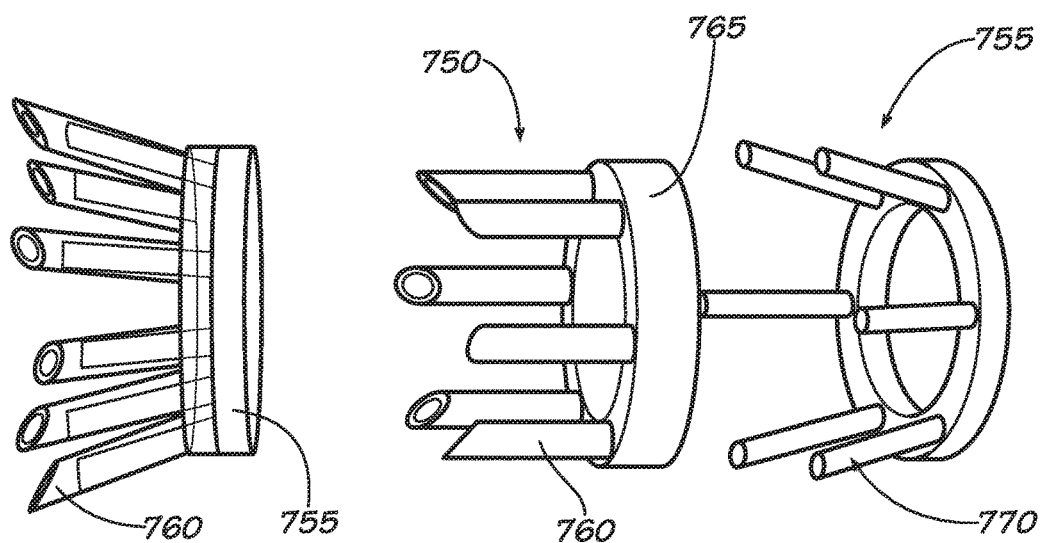

FIGS. 10B-10G illustrate various example embodiments of pinned supporting elements having multiple pins or needle members extending therefrom coordinating with various closing element embodiments. FIGS. 10B-10C illustrate one embodiment including a flexible sleeve 750 and a rigid guide 755. According to this embodiment, a closing element is provided by the flexible sleeve 750 having flexible pins or needle members 760 that extend at approximate right angles to the base 765 of the flexible sleeve 750, while the rigid guide 755 has guide pins 770 that angle outward from its base, as shown in FIG. 10C. Thus, during delivery, the guide pins 770 of the rigid guide 755 are inserted into the pins or needle members 760 of the flexible sleeve 750, causing the flexible pins or needle members 760 to deform and spread open (radially outward). The flexible sleeve 750 having the rigid guide 755 is inserted into the tissue wall and approximately surrounding the puncture site. When an inward radial force is desired, the rigid guide 755 is removed and the flexible pins or needle members of the flexible sleeve 750 return to their straight configuration, which in turn causes the tissue to be urged inward to facilitate closing the puncture site, as shown in FIG. 10C. The material of the flexible sleeve 750 should thus be formed from a material having at least partially elastic properties, but having a strength greater than the tissue to allow the flexible sleeve 750 to rebound to its natural state.

Figure 10D:
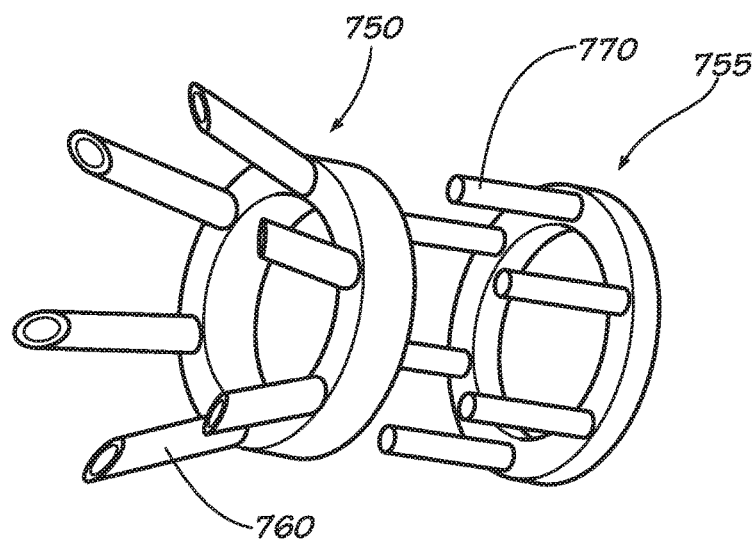

FIGS. 10D-10E illustrate another embodiment having a flexible sleeve 750 and rigid guide 755. However, according to this embodiment, the supporting element is provided by flexible pins or needle members 760 of the flexible sleeve 750 naturally in an open or expanded state, and the closing element is provided by the guide pins 770 of the rigid guide 755 formed at an approximate right angles or angled inward (at least relative to the open angle of the flexible pins or needle members 760). Thus, in this embodiment, during delivery, the flexible sleeve 750 is first inserted through the tissue wall to support and stabilize the tissue, and the rigid guide 750 is inserted into the flexible sleeve 750 when an inward radial force is desired, such as when closing the puncture site, as shown in FIG. 10E.

FIGS. 10F-10G illustrate another embodiment including a pinned supporting element. According to this embodiment, pivotable pins or needle members 775 of the supporting element extend within a base 780 of the closing element having grooves or channels 785 defined in an inner surface of the base 780, which define a path along which the pivotable pins or needle members 775 selectively travel. In use, during insertion into the tissue, the pivotable pins or needle members 775 of the supporting element may be in a first position as defined by the grooves or channels 785 that causes the pivotable pins or needle members 775 to be in an open or expanded state, as shown in FIG. 10F. When rotating the base 780 of the closing element (or otherwise causing movement of the pivotable pins or needle members 775 of the supporting element with respect to the grooves or channels 785), the grooves or channels 785 cause the pivotable pins or needle members 775 to compress inward, as shown in FIG. 10G, thus exerting an inward radial force on the tissue, such as when desiring to close the puncture site. It is appreciated that the supporting members described with reference to FIGS. 10A-10G may also be adapted to be utilized instead of an inner coil, providing the means for closing the tissue puncture site by inward radial forces.

Figure 10H:
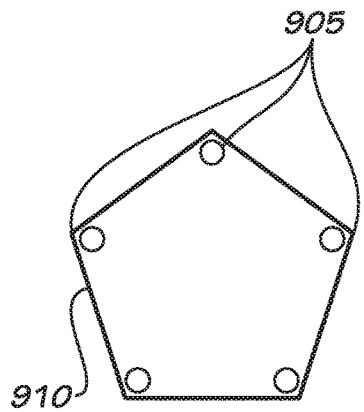
Figure 10I:
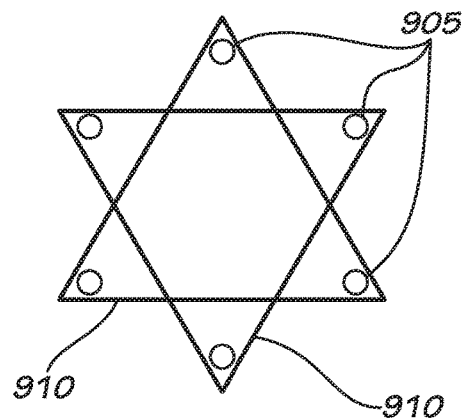

In a further embodiment, shown in an overhead view in FIGS. 10H and 10I, a series of pins 905 or anchors may be delivered into the tissue around the site of a puncture as the supporting element. These pins may then be selectively connected by one or several elastic bands 910 as the closing element. In FIG. 10H, five pins 905 of the supporting element encompassing the puncture site extend from the tissue surface to coordinate with one band 910 of the closing element. In FIG. 10I, six pins 905 of the supporting element encompassing the puncture site extend from the tissue surface to coordinate with two bands 910 of the closing element in an alternating pattern. It is appreciated that any number of pins and bands may be used in the invention to coordinate inward sealing pressure on the tissue puncture.

In this embodiment, the closing elements, the bands 910, are not inserted into the tissue. During delivery, these elastic bands are maintained in an extended state. When the pins 905 are in place, partially or completely in the tissue encompassing the puncture site, delivery tools which maintain the elastic band 910 closing elements in an extended position can be released, therefore allowing the elastic band 910 closure elements to recoil to their normal geometry around the pins 905. The mechanical recoil of the band 910 and the pattern of the pins 905 around the site of the puncture will then generate an inward compression radially toward the puncture site through the tissue, closing the puncture orifice, preventing fluid or blood loss.

Figure 10J:
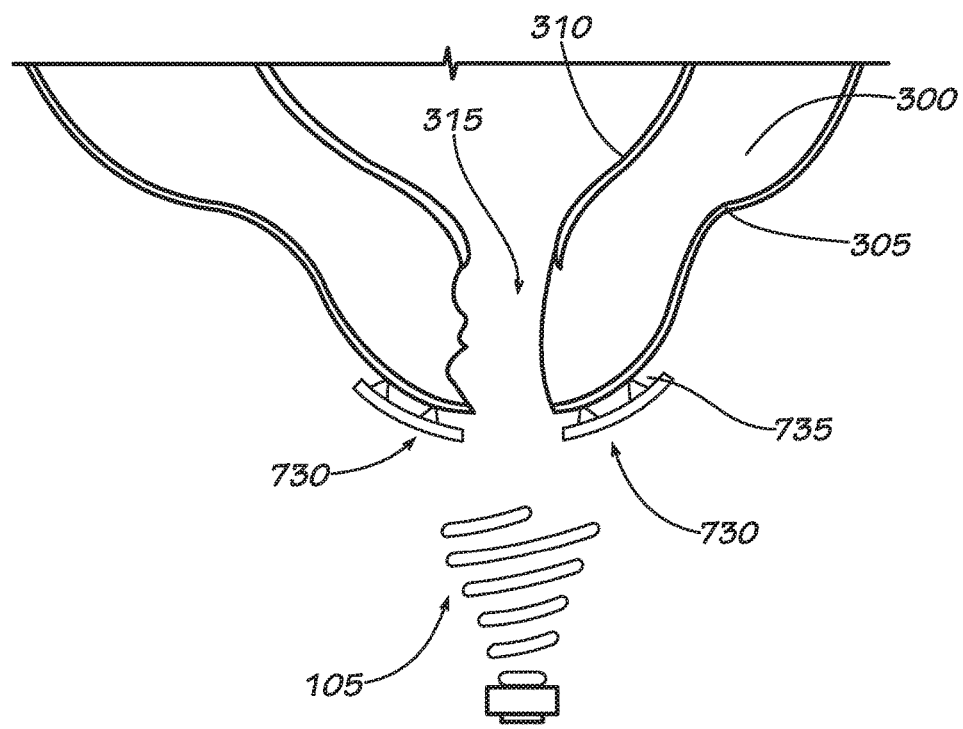

FIG. 10J illustrates one or more tissue supporting elements 730 adapted for placement on or into a surface of the tissue wall 300 proximate a puncture site 315, according to one embodiment. Surface supporting elements 730 may be designed in a number of configurations suitable to allow placing and securing to a tissue wall 300. For example, according to one embodiment, surface supporting elements 730 may be configured as one or more butterfly bandage or clip elements adapted to be placed across the tissue wall 300, such as at least partially across the perimeter of the puncture 315 or along the tissue wall 300 proximate the puncture 315. Surface supporting elements 730 may further include one or more securing members 735 adapted to facilitate securing to the tissue wall, such as, but not limited to, one or more teeth, prongs, pins, sutures, clips, etc.

It is appreciated that, according to various embodiments, the supporting elements 730 are adapted for placement on the outer surface 305 and/or the inner surface 310 of the tissue wall 300. In some embodiments, the surface supporting elements 730 may be formed, at least partially, from a biocompatible metal, a metal alloy, and/or a substantially rigid biocompatible polymer, or a combination thereof. In other embodiments, the surface supporting elements 730 may be formed, at least partially, from a non-rigid material, such as an biocompatible elastomeric polymer. Similar to that described with reference to FIGS. 1-4, a coiled closure device 105 may be inserted through the puncture 315, past the one or more surface supporting elements 730, and into the tissue wall 300 to compress the tissue and substantially close the puncture 315.

It is appreciated that the aforementioned supporting elements described with reference to FIGS. 10A-10J are provided for illustrative purposes and are not intended to be limiting. Any other suitable supporting element adapted to provide support to a tissue wall may be provided, including, but not limited to, suture, an adhesive member or bandage (e.g., a butterfly bandage, etc.), a mesh member (e.g., a mesh that can be adhered to the puncture surface and through which the coiled closure device 105 can be inserted, etc.), a compressive band or compression bandage (e.g., an elastomeric band placed around an apex-shaped tissue, such as a cardiac apex, etc.), and the like.

Figure 11A:
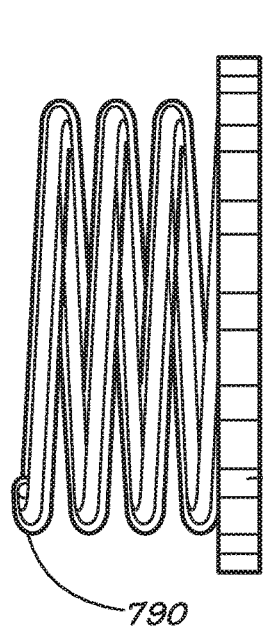
FIGS. 11A-11B illustrate side views of example outer coils and coiled closure devices with bored interiors, in accordance with various embodiments of the invention.
Figure 11B:
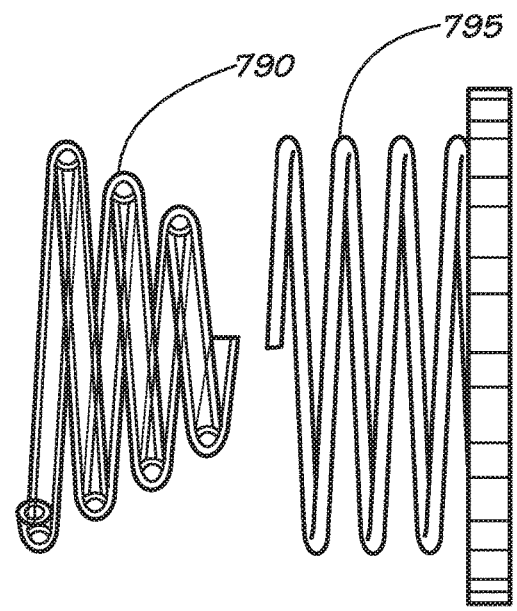

FIGS. 11A and 11B illustrate yet another embodiment of a closure device. According to this embodiment, an elastic hollow coiled member 790 has a natural state that defines a coil with an increasing radius, such as described with reference to FIG. 1. A coiled guide 795 includes a coil having a substantially constant radius and adapted to fit within the hollow coiled member 790. The constant radius of the coiled guide 795 causes the elastic hollow coiled member 790 to expand (increasing its smaller diameter) when inserted therethrough. Thus, during use, the coiled guide 795 is inserted into the elastic hollow coiled member 790, and both are inserted into the tissue at or near a puncture site. When an inward radial force is desired, the coiled guide 795 can be removed, causing at least a portion of the elastic hollow coiled member 790 to retract to its smaller diameter and cause an inward force on the tissue. It is appreciated that these elastic coiled member 790 and coiled guide 795 aspects can apply to an outer coil, an inner coil, or both, as are described with reference to FIG. 1.

Figure 12A:
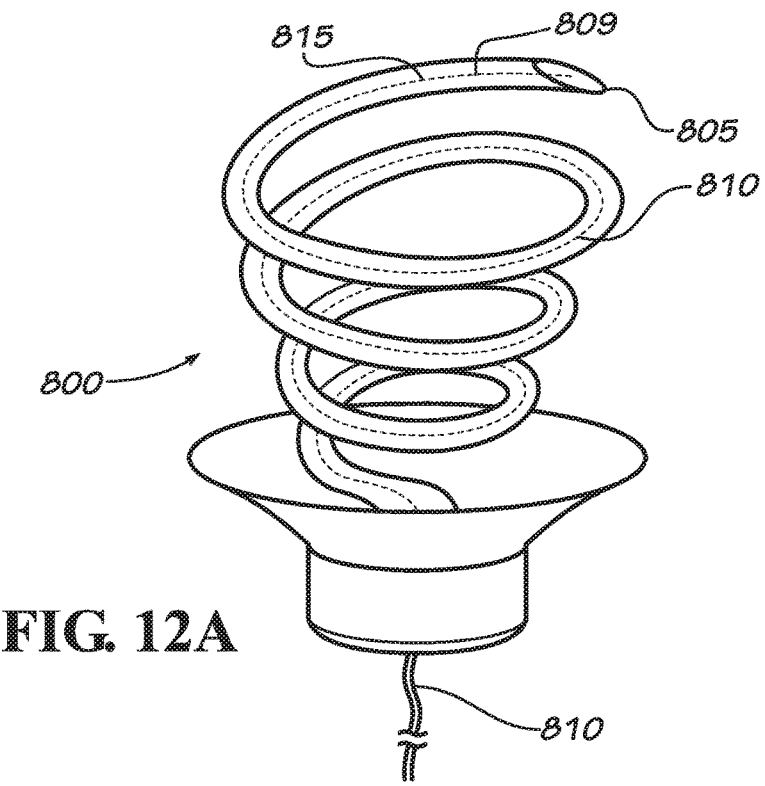
FIG. 12A illustrates views of an outer coil having a bore formed through the coil and a suture threaded therethrough for use in sealing the tissue wall, in accordance with one embodiment of the invention.

FIG. 12A illustrates a perspective view of an outer coil having a hollow bore formed through the coil member and a suture threaded therethrough for use in sealing the tissue wall, instead of using a coiled securing device, in accordance with one embodiment of the invention. According to this embodiment, an outer coil 800, similar to the outer coil 110 described with reference to FIGS. 1-4, is formed with a hollow bore 805 or passageway extending through the coil member from its proximal end 807 and exiting its distal end 809. It is appreciated that the outer coil 800 may have an increasing radius or may have a substantially constant radius, according to different embodiments.

The hollow bore 805 is adapted to receive suture 810 therein, whereby the suture 810 is intended to remain within a tissue wall when the outer coil 800 is removed. As shown in FIG. 12A, the suture 810 may extend from the proximal end of the outer coil 800, such as through an opening in the flange that is in communication with the hollow bore 805, to allow manipulating and securing the suture 810 when left behind in a tissue wall. According to one embodiment, the suture 810 may be pre-threaded through the hollow bore 805 prior to insertion of the outer coil 800 into a tissue wall, which may be performed during manufacturing or prior to distribution. In another embodiment, the suture 810 may be threaded manually by the operator either prior to inserting the outer coil 800 into a tissue wall or after insertion and prior to removal of the outer coil 800 from a tissue wall.

According to one embodiment, the suture 810 may include a securing member 815 dimensioned to fit within the hollow bore 805 and adapted to engage an inner surface (or other portion) of a tissue wall when the suture 810 is released from the bore 805. The securing member 815 may be configured in any suitable configuration, such as, but not limited to, a flat tab, a plug, one or more hooks, one or more prongs, one or more barbs, other interfering ends, and the like. Accordingly, when removing the outer coil 800 of this embodiment, the suture 810 is urged from the hollow bore 805 and will remain within the tissue wall. The suture 810 will remain in a coiled arrangement within the tissue wall, generally following the same path as the outer coil 800 as it is rotatably withdrawn from the tissue wall.

Figure 12B:
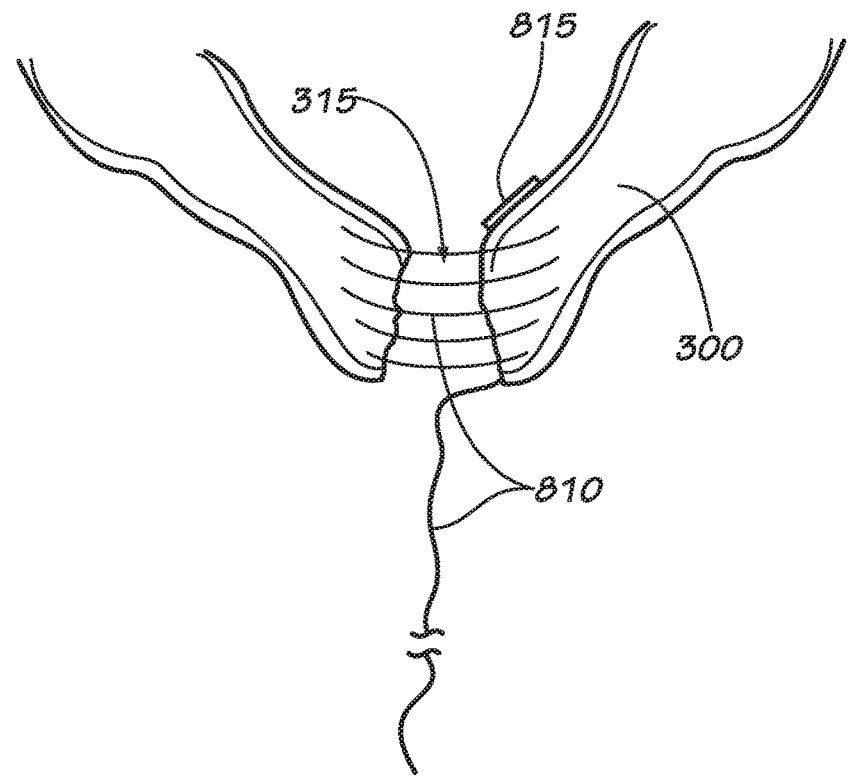
FIGS. 12B-12C illustrate cross-sectional views of a suture left behind in a tissue wall upon removing an outer coil, in accordance with one embodiment of the invention.
Figure 12C:
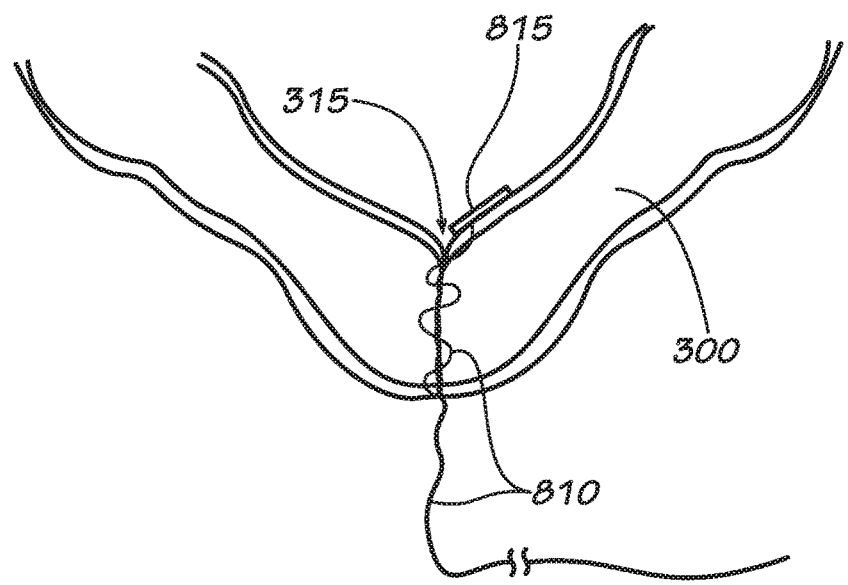

FIGS. 12B and 12C illustrate example cross-sectional views of the suture 810 left behind in a tissue wall 300 upon removing the outer coil 800. With reference to FIG. 12B, the suture 810 is shown in a loose state prior to tightening within the tissue wall 300 and prior to substantially sealing the puncture 315. FIG. 9B illustrates the same suture 810 in a tightened state after having tightened the suture 810 to substantially close the puncture 315. The suture 810 may be retained within the tissue wall 300 by the resistance applied by the securing element 815, as described with reference to FIG. 8. In the embodiment shown, the securing element 815 is urged against the inner surface 310 of the tissue wall 300. However, in other embodiments, the securing element 815 may be lodged at an intermediate position within the tissue wall 300 or at an intermediate position within the puncture 315 (e.g., such as if configured as a hook, barb, or plug). Pulling the proximal end of the suture 810 will tighten the suture within the tissue wall 300 and close the puncture 315.

Examples in Use:

One example embodiment of using a coiled closure device may be in combination with an outer coil device and a conduit device. In this example, an outer coil 110 is inserted into a tissue wall. After inserting the outer coil 110 at least partially through the tissue wall, a coring device may be passed through the approximate center of the outer coil 110 to puncture the tissue wall and optionally remove a portion thereof. After defining a puncture through the tissue wall, a conduit may be inserted therethrough, providing fluid communication between the inner surface and the outer surface of the tissue wall. For example, the conduit may be utilized to provide conduit access into a ventricle if the tissue wall is a cardiac apex. The increasing radius of the outer coil 110 acts to compress the tissue inwardly to seal against the conduit. Upon removing the conduit, which may be performed during and/or after the corresponding surgical procedure, a coiled closure device 105 may be rotatably inserted through the approximate center of the outer coil 110 (through the opening 117 of the flange 115) and at least partially through the tissue wall. Centering the coiled closure device 105 within the flange 115 will serve to orient the coiled closure device 105 to substantially surround the puncture previously created in the tissue wall. The increasing radius of the coiled closure device 105, in combination with its reduced coil diameters relative to the outer coil 110, allow the coiled closure device 105 to further compress the tissue wall and substantially close the puncture, minimizing or eliminating fluid flow therethrough. In some circumstances, the outer coil 110 may be removed, leaving the coiled closure device 105 within the tissue wall and substantially sealing the puncture.

According to another example of using a coiled closure device 105, the coiled closure device 105 may be inserted at least partially through a tissue wall without the use of an outer coil, but instead with the use of one or more different supporting elements, such as are described with reference to FIGS. 10A-10J. In this embodiment, a puncture may be formed through a tissue wall and a supporting element inserted or placed on the tissue wall to prevent further tearing while the puncture is utilized. Access through the tissue wall may be achieved without a conduit or with the insertion of a conduit, such as is described above. When the puncture is to be closed, the coiled closure device 105 may be inserted at least partially through the tissue wall and substantially surrounding the puncture. The increasing radius of the coiled closure device 105 allows the coiled closure device 105 to compress the tissue wall and substantially close the puncture, minimizing or eliminating fluid flow therethrough. In one embodiment, the coiled closure device 105 is inserted while the supporting element remains within the tissue wall. However, in other embodiments, the coiled closure device 105 may be inserted after removal of the supporting elements.

According to yet another example of using a coiled closure device 105, the coiled closure device 105 may be inserted at least partially through a tissue wall without the use of an outer coil or other supporting elements. In this embodiment, a puncture may be formed through a tissue wall and access through the tissue wall achieved (e.g., with or without a conduit). When the puncture is to be closed, the coiled closure device 105 may be inserted at least partially through the tissue wall and substantially surrounding the puncture. The increasing radius of the coiled closure device 105 allows the coiled closure device 105 to compress the tissue wall and substantially close the puncture, minimizing or eliminating fluid flow therethrough.

In any of the prior examples of using a coiled closure device 105, a delivery instrument, such as the delivery instrument 130 described with reference to FIGS. 1 and 5A-5D, may be utilized to rotatably insert and to rotatably remove the coiled closure device 105 and the outer coil 110 if used. Accordingly, the delivery instrument 130 may releasably engage the proximal end of the coil members, allowing a user to supply the necessary rotational force thereto. As described above with reference to FIGS. 5A-5D, the delivery instrument 130 may include means for preventing over or under insertion of the coil and thus undesirable damage to the tissue wall. FIGS. 5C and 5D illustrate different embodiments of preventing over torquing or over insertion of the coiled closure device. When using this tool and the closing coil moves into the tissue to a predetermined depth, the main shaft 520 of the delivery device becomes displaced and separated from the handle 530 preventing any further turning or insertion of the coiled closure device. Other embodiments describe a ratchet-based mechanism to prevent over torquing of the coiled closure device into the tissue. Over torquing beyond a pre-selected calibration would transfer the force through the shaft bending a calibrated plate or pin resulting in the dis-engagement of the handle of the delivery device from the main shaft, therefore, not allowing for further transfer of motion.

Many modifications and other embodiments of the invention will come to mind to one skilled in the art to which this invention pertains and having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A system for closing a puncture formed in a tissue wall, the system comprising:
   a supporting device comprising:
      a first coil adapted for at least partial insertion into the tissue wall such that at least a portion of the first coil is disposed between a first surface and an opposite second surface of the tissue wall and proximate the puncture to inhibit expansion of the puncture; and
      a first flange fixedly attached to the first coil and defining a central opening positioned along a central axis of the supporting device, the first flange adapted for positioning against the first surface of the tissue wall; and
   a closing device comprising:
      a second coil adapted for at least partial insertion through the central opening of the first flange and at least partial insertion into the tissue wall such that at least a portion of the second coil is disposed between the first surface and the second surface of the tissue wall and proximate the puncture to close the puncture; and a second flange fixedly attached to the second coil, the second flange adapted for at least partial insertion through the central opening of the first flange and positioning against the first surface of the tissue wall, wherein a minimum helical diameter of the first coil is greater than an the internal diameter of the central opening, wherein a maximum helical diameter of the second coil is less than the internal diameter of the central opening, and wherein a maximum outer diameter of the second flange is less than the internal diameter of the central opening.

2. The system of claim 1, wherein the first coil is adapted for compressing at least a portion of the tissue wall inward toward a central axis of the first coil when the first coil is inserted at least partially into the tissue wall.

3. The system of claim 1, wherein the first coil has a proximal end and a distal end, and wherein the first flange is fixedly attached to the proximal end of the first coil.

4. The system of claim 3, wherein a helical diameter of the first coil increases along at least a portion of the first coil in a direction from the proximal end toward the distal end of the first coil.

5. The system of claim 3, wherein a helical diameter of the first coil is constant along at least a portion of the first coil.

6. The system of claim 3, wherein the first coil has a first helical diameter at the proximal end of the first coil and a second helical diameter at the distal end of the first coil, wherein a maximum outer diameter of the first flange is greater than the first helical diameter, and wherein the maximum outer diameter of the first flange is less than the second helical diameter.

7. The system of claim 3, wherein the first coil comprises a sharpened tip positioned at the distal end of the first coil and adapted for piercing the first surface of the tissue wall.

8. The system of claim 3, wherein a central axis of the first coil is coaxial with the central axis of the supporting device.

9. The system of claim 1, wherein the second coil is adapted for compressing at least a portion of the tissue wall inward toward a central axis of the second coil when the second coil is inserted at least partially into the tissue wall.

10. The system of claim 1, wherein the second coil has a proximal end and a distal end, and wherein the second flange is fixedly attached to the proximal end of the second coil.

11. The system of claim 10, wherein a helical diameter of the second coil increases along at least a portion of the second coil in a direction from the proximal end toward the distal end of the second coil.

12. The system of claim 10, wherein a helical diameter of the second coil is constant along at least a portion of the second coil.

13. The system of claim 10, wherein the second coil has a first helical diameter at the proximal end of the second coil and a second helical diameter at the distal end of the second coil, wherein a maximum outer diameter of the second flange is greater than the first helical diameter, and wherein the maximum outer diameter of the second flange is less than the second helical diameter.

14. The system of claim 10, wherein the second coil comprises a sharpened tip positioned at the distal end of the second coil and adapted for piercing the first surface of the tissue wall.

15. A system for closing a puncture formed in a tissue wall, the system comprising:

a supporting device comprising:
a first coil adapted for at least partial insertion into the tissue wall such that at least a portion of the first coil is disposed between a first surface and an opposite second surface of the tissue wall, the first coil having a proximal end and a distal end; and a first flange fixedly attached to the proximal end of the first coil and defining a central opening positioned along a central axis of the supporting device, the first flange adapted for positioning against the first surface of the tissue wall; and a closing device comprising:
a second coil adapted for at least partial insertion through the central opening of the first flange and at least partial insertion into the tissue wall such that at least a portion of the second coil is disposed between the first surface and the second surface of the tissue wall and for compressing at least a portion of the tissue wall inward toward a central axis of the second coil when the second coil is inserted at least partially into the tissue wall, the second coil having a proximal end and a distal end; and a second flange fixedly attached to the proximal end the second coil, the second flange adapted for at least partial insertion through the central opening of the first flange and positioning against the first surface of the tissue wall, wherein a minimum helical diameter of the first coil is greater than an the internal diameter of the central opening, wherein a maximum helical diameter of the second coil is less than the internal diameter of the central opening, and wherein a maximum outer diameter of the second flange is less than the internal diameter of the central opening.

* * * * *